US010247655B2

(12) United States Patent
Smith et al.

(10) Patent No.: US 10,247,655 B2
(45) Date of Patent: Apr. 2, 2019

(54) MICROFLUIDIC DEVICES AND SYSTEMS

(71) Applicant: Sphere Fluidics Limited, Babraham Cambridge, Cambridgeshire (GB)

(72) Inventors: Clive A. Smith, Babraham Cambridge (GB); Xin Li, Babraham Cambridge (GB); Karine Enesa, Babraham Cambridge (GB); Xin Liu, Babraham Cambridge (GB); Frank F. Craig, Babraham Cambridge (GB); Graeme Whyte, Uttenreuth (DE)

(73) Assignee: SPHERE FLUIDICS LIMITED, Babraham, Cambridge, Cambridgeshire (GB)

( * ) Notice: Subject to any disclaimer, the term of this patent is extended or adjusted under 35 U.S.C. 154(b) by 414 days.

(21) Appl. No.: 14/907,867

(22) PCT Filed: Jul. 30, 2014

(86) PCT No.: PCT/GB2014/052332
§ 371 (c)(1),
(2) Date: Jan. 27, 2016

(87) PCT Pub. No.: WO2015/015199
PCT Pub. Date: Feb. 5, 2015

(65) Prior Publication Data
US 2016/0252446 A1    Sep. 1, 2016

(30) Foreign Application Priority Data
Jul. 30, 2013  (GB) .................................. 1313582.7

(51) Int. Cl.
*G01N 15/14* (2006.01)
*B01L 3/00* (2006.01)
(Continued)

(52) U.S. Cl.
CPC .... *G01N 15/1434* (2013.01); *B01L 3/502784* (2013.01); *C12Q 1/04* (2013.01);
(Continued)

(58) Field of Classification Search
CPC ..... B01L 2200/0652; B01L 2200/0673; B01L 3/502784; G01N 15/1425; G01N 15/1434;
(Continued)

(56) References Cited

U.S. PATENT DOCUMENTS 5,587,153 A    12/1996  Angelone, Jr. et al.
6,017,546 A    1/2000   Glover
(Continued)

FOREIGN PATENT DOCUMENTS

WO    20040038363 A2    5/2004
WO    2005099661 A1    10/2005
(Continued)

OTHER PUBLICATIONS

Budwig. Experiments in Fluids, vol. 17, 1994, pp. 350-355.*
(Continued)

*Primary Examiner* — Maureen Wallenhorst
(74) *Attorney, Agent, or Firm* — Renner Kenner Greive Bobak Taylor & Weber

(57) ABSTRACT

A method of label-free cell or particle sorting in a microfluidic device includes providing a stream of aqueous droplets in oil in a channel of the microfluidic device, wherein at least some of the droplets include cells or particles and illuminating the stream from a first direction. Then, one detects scattered light from cells or particles within said aqueous droplets in a second direction. Next, one determines a number of the cells or particles in each droplet from the scattered light and sorts the aqueous droplets into differentiated streams. Notably, the refractive index of said oil is
(Continued)

modified to closely match a refractive index of the aqueous droplets to reduce light scattered from boundaries of the droplets. A volume of the droplets can also controlled.

13 Claims, 9 Drawing Sheets

(51) Int. Cl.
  *C12Q 1/04* (2006.01)
  *C12Q 1/06* (2006.01)
  *G01N 21/49* (2006.01)
  *G01N 15/00* (2006.01)

(52) U.S. Cl.
  CPC ........... *C12Q 1/06* (2013.01); *G01N 15/1425* (2013.01); *B01L 2200/0652* (2013.01); *B01L 2200/0673* (2013.01); *G01N 21/49* (2013.01); *G01N 2015/0065* (2013.01); *G01N 2015/149* (2013.01); *Y10T 436/2575* (2015.01)

(58) Field of Classification Search
  CPC ..... G01N 2015/0065; G01N 2015/149; G01N 21/47; G01N 21/49; G01N 21/53; G01N 21/532; Y10T 436/25; Y10T 436/2575; C12Q 1/02; C12Q 1/025; C12Q 1/04; C12Q 1/06; C12Q 1/18
  USPC .... 436/63, 164, 174, 180; 422/82.05, 82.09, 422/502; 435/29, 32, 34, 39, 287.1, 435/287.3, 288.7
  See application file for complete search history.

(56) References Cited

U.S. PATENT DOCUMENTS

| | | | |
|---|---|---|---|
| 6,379,682 | B1 | 4/2002 | Tchinnis et al. |
| 9,513,207 | B2* | 12/2016 | Smith ............... B01L 3/502784 |
| 2002/0143072 | A1* | 10/2002 | Aust ...................... A61K 8/062 |
| | | | 516/98 |
| 2002/0172703 | A1 | 11/2002 | Lorant et al. |
| 2004/0081633 | A1 | 4/2004 | Mercier et al. |
| 2005/0087122 | A1 | 4/2005 | Ismagliov et al. |
| 2005/0099661 | A1 | 5/2005 | Tien |
| 2007/0275415 | A1 | 11/2007 | Srinivasan et al. |
| 2008/0053205 | A1 | 3/2008 | Pollack et al. |
| 2017/0175174 | A1* | 6/2017 | Chiu .................... C12Q 1/6816 |

FOREIGN PATENT DOCUMENTS

| | | |
|---|---|---|
| WO | 20080063227 A2 | 5/2008 |
| WO | 20090050512 A2 | 4/2009 |

OTHER PUBLICATIONS

Daviel R. Gossett, et al., "Label-Free cell separation and sorting in microfluidic systems", Analytical and Bioanalytical Chemistry, Springer, Berlin, DE; vol. 397, No. 8; Apr. 25, 2010, pp. 3249-3267, XP019839258, ISSN: 1618-2650, p. 3263.

Intellectual Property Office; UK Search Report; dated Mar. 19, 2014; 5 Pages.

* cited by examiner

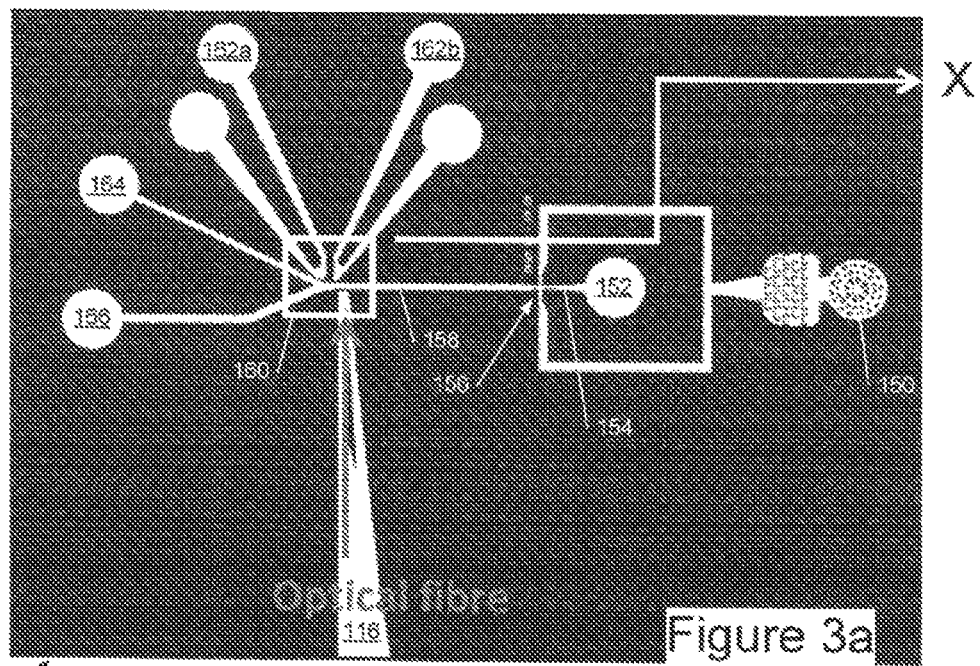
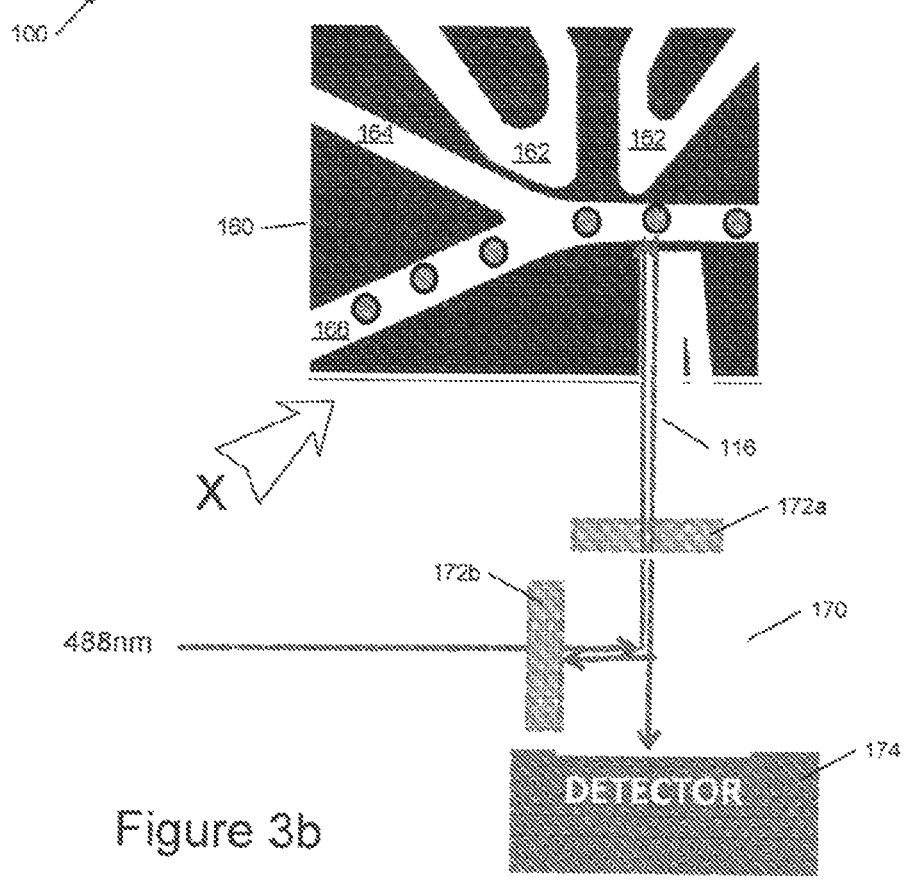
Figure 3a
Figure 3b

MICROFLUIDIC DEVICES AND SYSTEMS

FIELD OF THE INVENTION

This invention relates to microfluidic devices and more particularly to techniques for label-free cell and particle sorting in microfluidic devices. In other aspects the invention relates to improved techniques for performing a biological, in particular a cellular proliferation assay. The invention still further relates to control systems for microfluidic devices.

BACKGROUND TO THE INVENTION

In this specification we are concerned with emulsions comprising microdroplets of water in oil, generally surfactant-stabilised, used in a microfluidic device. One or more biological entities such as one or more living cells or particles may be incorporated into each droplet and then experiments performed within the droplet, for example to perform a biological assay. The technique is promising because the volume of a droplet is very small, typically in the order of picoliters, and thus the volume of biological material needed is small, and because microdroplets can be generated and processed, for example directly within the microfluidic device, at rates in excess of several thousands per second. Further, integrated active elements on the microfluidic device can be used to control individual droplets—for example we have previously described in WO2009/050512, technology which enables the extraction on-chip of the contents of microdroplets by incorporating them into a continuous stream. Other general background prior art on microdroplets can be found in patents/applications in the name of RainDance Technologies Inc., for example WO2008/063227.

Typically the oil composition comprises a fluorous and/or mineral oil and, preferably, a surfactant, for example at around 0.5-5% vol/vol. Use of a fluorous oil is particularly advantageous when the microdroplets contain living entities because fluorous oil is good at transporting oxygen to the microdroplets. The surfactant may be either polymeric or small molecule; for example surfactants derived from block co-polymers of perfluoroethers such as Krytox™ or polyethylene glycol (PEG) may be used.

General background prior art relating to emulsions for other applications (generally cosmetics) can be found in the following: U.S. Pat. Nos. 5,587,153; 6,017,546; WO2005/099661; US2004/081633; U.S. Pat. No. 6,379,682; US2002/172703. Further background prior art can be found in: US2005/087122; WO2004/038363; US2008/053205; and US2007/0275415.

The material or analyte within a microdroplet may comprise, for example, DNA, protein, peptide, beads, particles, crystals, micelles, macromolecules, material for an enzymatic assay, organelles, an organism such as cell for example a mammalian cell, yeast cell, algal cell or bacterium, a virus, a prion and so forth. Typically a droplet has a diameter in the range 1-120 µm although droplets may be larger (or smaller), giving a volume in the range nanoliters to femtoliters. In this specification we are particularly, but not exclusively concerned with microdroplets containing cells—the techniques we describe are particularly useful for cells but may, in principle, be applied to microdroplets containing other organisms/biological entities, beads or particles.

Hitherto microdroplet-based processing of cells has generally been limited to labelling the cells with a fluorescent marker activated under certain circumstances. Then, as a microdroplet passes through a channel of the microfluidic device the microdroplet is illuminated by a laser and fluorescence or the absence of fluorescence is detected and the microdroplet containing the cell is directed accordingly. The inventors have recognised, however, that it is possible to improve upon this technique.

SUMMARY OF THE INVENTION

According to a first aspect of the invention there is therefore provided a method of label-free cell or particle sorting or assaying in a microfluidic device, the method comprising: providing a stream of aqueous droplets in oil in a channel of said microfluidic device, wherein at least some of said droplets include cells or particles; illuminating said stream from a first direction; detecting light from cells or particles within said aqueous droplets in a second direction; determining a property of said cells or particles in each droplet from said detected light; and sorting said aqueous droplets into one of a plurality of differentiated streams responsive to said determined property; the method further comprising modifying a refractive index of said oil to more closely match a refractive index of said aqueous droplets to reduce light scattered from boundaries of said droplets.

In some preferred embodiments the method comprises determining a number of cells and/or particles in each droplet from the detected light. More particularly, however, the techniques we describe enable an assay to be performed by visualising and counting individual cells (or particles) within a droplet.

Embodiments of the technique enable a detection system, surprisingly, to "see" light from cells or particles within a microdroplet despite their small size and even the droplets themselves being relatively difficult to visualise. This in turn facilitates new types of biological assay, for example a proliferation assay. In such a proliferation assay cells may be cultured within the microdroplets in the presence of a drug intended to inhibit cell proliferation and then the cells in each droplet counted to determine whether or not cells have been able to grow in the presence of the drug. In this way, for example, the resistance of a bacterium to antibiotics may be determined, extracting a very small population of bacteria with this phenotype from a population of greater than 100 million or 1 billion bacteria, making use of the high droplet throughput rate achievable in a microfluidic device.

In some embodiments of the technique the light detected is scattered light from the cells; in others it is fluorescent light from the cells. For example, antigens may be labelled on the surface of the cell(s) with a fluorescently labelled antibody or phage, so that the cells are much brighter than the fluorescently labelled analyte in the droplet. Similarly, with embodiments of the techniques we describe it is easier to detect the binding of an unlabelled antibody or phage producing a functional effect (for example as an agonist, partial agonist, antagonist or partial antagonist) on a cell surface protein that, in turn, is detected by a fluorescent signal either internal to the cell or (homogeneously) within the droplet.

Furthermore, embodiments of the technique make it possible to improve the sensitivity of detection of molecular binding to a target by measuring a shift in the wavelength and/or an increase or decrease in emission from the target particle/entity. Thus, broadly speaking, embodiments of the method employ the techniques we describe to provide an improved, more sensitive/accurate fluorescence assay of the contents of a droplet, in particular cells within a droplet—for example to identify an agonist, partial agonist, antagonist, or partial antagonist.

Interestingly, embodiments of the technique also facilitate differentiation between live and dead cells: Live cells have an intact membrane which deflects light, but when cells die, they tend to lyse and break into small fragments. These small fragments tend to reflect less than intact cells, and our techniques enable this to be observed. Thus the determined property of a cell may be whether the cell is living or dead.

It is desirable to achieve relatively high intensity illumination across the width of a microdroplet (which may be up to the width of the channel), and in embodiments this is achieved by employing a fibre optic adjacent the channel with a light-guiding dimension at least equal to that of the channel to illuminate the channel from a first direction. The light from cells within the droplets may then be detected from a second direction, preferably different, in particular substantially orthogonal to the first direction. In some preferred embodiments the scattered light is detected using a photomultiplier (or "silicon photomultiplier") which has the desirable high sensitivity. In principle imaging apparatus could be employed but this apparatus would need to be sensitive, fast and would require fast processing of the captured image frames.

In other embodiments the method comprises illuminating with an optic fibre and detecting the reflected, back-scattered light, or fluorescence, in the opposite direction using the same fibre. This, advantageously, can remove the need for a microscope for viewing the scattered light.

In embodiments the scattered light/fluorescence thus comprises light from the plurality of cells (when present) within a droplet and thus represents a form of integrated response. Thus the determining of the number of cells in a droplet may comprise determining whether the number of cells falls above or below a threshold number, for example 20, or whether the number of cells is within one of a plurality of predetermined ranges (the number of cells within a droplet generally follows a Poisson distribution). In preferred embodiments an integrated intensity of the scattered light from a droplet over time is determined to determine the number of cells within the droplet. Additionally or alternatively, however, the width of a peak of detected light from the droplet and/or the area (above a baseline) of a peak of detected light from the droplet may be measured to determine the number of cells within the droplet.

Apart from the proliferation assays mentioned above, the ability to accurately count cells in a droplet have many other applications, as the skilled person will recognise.

For example it can be useful to discriminate between droplets containing a single cell and droplets containing zero cells and/or droplets containing more than cell. The ability to guarantee a single cell per droplets is useful for example in analysing single plasma or B-cells for antibody production or ensuring a preparation of single cells for making hybridomas.

In some embodiments modifying the refractive index may substantially match the refractive indices of the droplet and the oil so that the boundary of the droplet is substantially invisible. However in other approaches the refractive indices are deliberately left with a slight mismatch in order to be able to visualise droplets separately to the cells, for example for use by another, droplet flow rate detection system.

It can be important to control the volume of each droplet, preferably so that the droplet volumes are substantially monodisperse. This is particularly the case where there is a relatively small number of cells per droplet, for example less than 5, 2 or 1 on average. This is because with, say, a single cell per droplet changes in the droplet volume will significantly change the concentration of substances in the environment of the cell within the droplet over time—for example the antibody concentration in an immunoassay detecting, say, antibody production through fluorescence, for example FRET (fluorescence resonance energy transfer).

In embodiments of the method, therefore, the scattered or fluorescent light from the cells or, alternatively, scattered light from the droplets themselves (where a separate illumination and/or scattered light detection system is employed to detect the droplets) is employed to measure a flow rate of the aqueous droplets in the channel. The volume of the droplets may then be controlled in response to the determined flow rate, for example by controlling a rate at which the oil and/or water is provided to a droplet generation structure, typically on the microfluidic device, such as a flow focus junction. (As the skilled person will be aware, in such a junction the aqueous medium flows along a channel and oil flows in from, in general, to opposite sides of the channel to cut off droplets of the aqueous medium within the oil—controlling the flow rate thus controls the volume of the droplets). The flow rate of the oil and/or aqueous medium may be controlled by controlling a pump, for example an air-pressure controlled pump.

In some preferred implementations, to determine the rate of passage of the aqueous droplets in the stream past a detection point in the channel a time-frequency transform is applied to the detected scattered light. This may comprise a discrete Fourier transform; in embodiments this may be implemented in hardware, for speed. With such an approach the droplet frequency appears as a fundamental frequency in frequency space even where the individual signals are noisy or absent (as can be the case when detecting droplets or cells within the droplets).

The skilled person will appreciate that this droplet-volume controlled technique may be employed independently of the above described label-free cell sorting.

Thus in a further aspect the invention provides a method of controlling a microfluidic device, the method comprising: providing a stream of aqueous droplets in oil in a channel of said microfluidic device; determining, using (scattered and/or fluorescent) light from said droplets or contents of said droplets, a rate of passage of said aqueous droplets in said stream past a point in said channel; and controlling a volume of said droplets responsive to said determined rate of passage to thereby regulate the volumes of the microdroplets. Preferably the method is label-free. Preferably the light is scattered light.

In a related aspect the invention provides a method of performing an assay in a channel of a microfluidic device, the method comprising: providing a stream of aqueous droplets in oil in a channel of said microfluidic device, wherein at least some of said droplets include entities; detecting (scattered and/or fluorescent) light from said droplets or from said entities within said droplets; and one or both of: performing said assay on the contents of said droplets using said detected light by index matching refractive indices of said aqueous droplets and oil; and controlling a volume of said droplets using said detected light.

In preferred embodiments of the method the assay is a biological assay, more particularly a proliferation assay. Preferably the biological entities comprise cells, more particularly micro-organisms (e.g. bacteria), and the assay comprises visualising and counting the entities within the droplets.

In embodiments a droplet has a diameter of less than 120, 100, 50, 20 or 10 µm; preferably a droplet production rate, which is related to droplet size, is at least 100 Hz, 1 KHz, 10 KHz or 50 KHz; preferably a droplet contains less than 100 bacteria (on average—the number generally follows a Poisson distribution), for example in a range 10-50 bacteria. These parameters facilitate screening large numbers, for example billions, of bacteria and allow access to a domain of operation of the microfluidic device which is difficult to access using conventional techniques in part because a fluorescent reporter will diffuse out of a droplet when the droplet is small and thus has a large surface area to volume ratio. By contrast the label-free technique we describe is able to sustain and grow bacteria in very small droplets generated at very high rates whilst avoiding some of the false positive detections which can arise with conventional techniques under such conditions which can mimic the proliferation of bacteria in the presence of an anti-bacterial substance.

As previously described the microfluidic device may include fibre optic illumination for the channel preferably embedded within a polymer forming the channel.

Thus in a further aspect the invention provides a control system for a microfluidic device, the control system comprising: optical apparatus to detect passage of a stream of aqueous droplets in oil through a channel of said microfluidic device; a signal processor, coupled to said optical apparatus, to determine a rate of flow of said droplets in said channel; and a controller, coupled to said signal processor, to control a flow rate of aqueous medium and/or oil forming said droplets responsive to said determined rate of flow to regulate the volumes of said droplets.

In a further aspect the invention provides a stream of emulsion in a microfluidic device, the stream of emulsion comprising aqueous droplets in oil, wherein said emulsion further comprises a refractive index modifying compound in the oil phase of the emulsion, wherein said refractive index modifying compound is substantially insoluble in said aqueous droplets, and wherein a refraction index of a combination of said refractive index modifying compound and said oil is closer to a refractive index of said aqueous droplets than a refractive index of said oil alone.

In preferred embodiments the refractive index modifying compound has a refractive index greater than 1.333 at a wavelength in the range 0.4 µm to 1.6 µm, for example 1 µm or 1.5 µm. In embodiments the refractive index modifying compound has a refractive index (at a wavelength/range as defined previously) greater than 1.379. Preferably the refractive index of the combination of oil and refractive index modifying compound (at a wavelength/range as previously defined) matches refractive index of an aqueous droplet to within 0.005, 0.001, 0.0005, 0.0003, 0.0002 or 0.0001.

As previously described, in preferred embodiments the oil comprises fluorous oil containing a fluorous surfactant, e.g. Pico-Surf™ 1 or Pico-Surf™ 2, to stabilise the droplets; preferably the aqueous droplets comprise a growth medium; some at least will contain cells or other biological entities. Optionally a droplet volume control system is also provided.

Although we have described aspects and embodiments of the invention for use in label-free cell and particle sorting it will be appreciated that the final, sorting step is not essential depending upon the application in which the techniques we describe is used.

In a further aspect the invention provides an emulsion for sorting droplets in a microfluidic device, the emulsion comprising: a discontinuous aqueous phase; and a continuous oil phase; wherein the aqueous phase comprises at least one analyte, the oil phase comprises a fluorous oil and a refractive index modifying compound comprising at least one aromatic ring, and the refractive index of the aqueous phase and the refractive index of the oil phase are substantially matched.

As used herein the term "refractive index" refers to a number that describes how radiation, e.g. light, propagates through a medium. The refractive index of an oil phase or an aqueous phase is preferably measured using a refractometer at the D-line of sodium at a wavelength of 589.3 nm.

In preferred emulsions of the present invention the refractive index of the aqueous phase is 1.333 or greater. Typically the refractive index of the aqueous phase is in the range 1.333 (de-ionised water at the D-line of sodium, 589.3 nm, taken from http://www.kayelaby.npl.co.uk/general_physics/2_5/2_5_8.html) to 1.3800. Preferably the refractive index of the aqueous phase is 1.333 to 1.3800, more preferably 1.333 to 1.3700 and still more preferably 1.333 to 1.3500.

In emulsions of the present invention the refractive index of the aqueous phase and the refractive index of the oil phase are substantially matched. This means that when a sample of the emulsion is illuminated with light that the majority of scattering occurs from analytes (e.g. particles or cells) present in the aqueous phase, rather than from the interface or boundary between the aqueous and oil phases. In preferred emulsions of the present invention the difference in the refractive index of the aqueous phase and the refractive index of the oil phase is 0 to 0.005, more preferably 0.001 to 0.0005, still more preferably 0.0005 to 0.0001 and yet more preferably 0.0001 to 0.00005.

The matching of the refractive indices of the phases in the emulsion of the present invention is achieved by matching the refractive index of the oil phase to the refractive index of the aqueous phase. The oil phase comprises a fluorous oil, a refractive index modifying compound and preferably a surfactant, especially preferably a fluorosurfactant. The refractive index of fluorous oils is generally less than the refractive index of deionised water (i.e. less than 1.333). Preferably, however, the fluorous oil, optionally containing 0.5-5% wt surfactant as described below, has a refractive index of 1.250 to 1.337, more preferably 1.280 to 1.335 and still more preferably 1.290 to 1.334. Advantageously a fluorous oil having a refractive index as close to 1.333 as possible is used since this means that the amount of refractive index modifying compound necessary to achieve index matching is minimised.

Preferably the fluorous oil present in the emulsions of the present invention has a boiling point of 100 to 250° C. and more preferably 120 to 230° C. Preferably the fluorous oil present in the emulsions of the present invention has a density of 1.50 to 2.50 g/ml, more preferably 1.70 to 2.30 g/ml and still more preferably 1.80 to 2.10 g/ml.

Preferably the fluorous oil present in the emulsion of the present invention is a fluorinated hydrocarbon, still more preferably a fluoroalkyl and yet more preferably a $C_6$-$C_{24}$ fluoroalkyl. The fluorinated hydrocarbon may be straight chained, branched or cyclic. The fluorinated hydrocarbon may be substituted or unsubstituted, but is preferably unsubstituted. The fluorous oil may be a partially fluorinated hydrocarbon or a perfluorinated hydrocarbon. Preferably, however, the fluorous oil is a perfluorinated hydrocarbon.

In particularly preferred emulsions of the present invention the fluorous oil comprises a compound of formula (I) or (II):

$$X_3C\text{—}(CX_2)_n\text{—}Z\text{—}(CX_2)_m\text{-}CX_3 \qquad (I)$$

wherein
each X is independently F, H, $C_{1-6}$ alkyl, $C_{1-6}$ fluoroalkyl, $C_{1-6}$ alkoxy or $C_{1-6}$ fluoroalkoxy, with the proviso that at least one X is F;
Z is $(CX_2)$ or NY;
Y is $(CX_2)_pCX_3$;
n is an integer from 1 to 8,
m is an integer from 1 to 8, and
p is 0 or an integer from 1 to 8

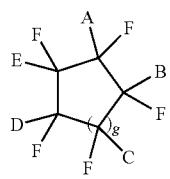

(II)

wherein
one or two carbon atoms in the ring, together with the atoms to which they are attached, are optionally replaced by a heteroatom;
g is an integer selected from 1, 2, 3 or 4;
A, B and C are each independently selected from F, H, $C_{1-6}$ alkyl, $C_{1-6}$ fluoroalkyl, $C_{1-6}$ alkoxy or $C_{1-6}$ fluoroalkoxy;
D and E are each independently selected from F, H, $C_{1-6}$ alkyl, $C_{1-6}$ fluoroalkyl, $C_{1-6}$ alkoxy or $C_{1-6}$ fluoroalkoxy or together with the carbon atoms to which they are attached, D and E form a fluorocycloalkyl ring system.

As used herein the term "alkyl" refers to saturated, straight chained, branched or cyclic groups. Alkyl groups may be substituted or unsubstituted. As used herein the term "fluoroalkyl" refers to saturated, straight chained, branched or cyclic alkyl groups in which one or more hydrogen atoms are replaced by an F atom. As used herein the term "alkoxy" refers to O-alkyl groups, wherein alkyl is as defined above. As used herein the term "fluoroalkoxy" refers to O-fluoroalkyl groups, wherein fluoroalkyl is as defined above. Examples of "heteroatoms" include N, S or O.

In emulsions of the present invention the fluorous oil may comprise one or more compounds of formula (I) and/or (II). Preferably, however, the emulsion comprises one compound of formula (I) or (II). In some emulsions compounds of formula (I) are preferred. Generally, however, compounds of formula (II) are preferred.

In preferred compounds of formula (I) at least 80% of the X groups present are F or $C_{1-6}$ fluoroalkyl and especially F. Thus in perfluoroctane, for example, there are 18 X groups present and all 18 are F. Thus 100% of the X groups present are F. In 3M Novec-7500 which has the structure (Ivi) shown below there are 14 X groups present and 13 of these are F or $C_{1-6}$ fluoroalkyl and 12 are F. Thus 93% of the X groups present are F or $C_{1-6}$ fluoroalkyl and 86% are F. In particularly preferred compounds of formula (I) 80-100% of the X groups present, and more preferably 85 to 100% of the X groups present are F or $C_{1-6}$ fluoroalkyl and especially F.

In some preferred fluorous oils of formula (I) each X is F. In other preferred fluorous oils of formula (I) at least one X group is $C_{1-6}$ fluoroalkyl. In other preferred fluorous oils of formula (I) at least one X group is $C_{1-6}$ alkoxy.

In further preferred fluorous oils of formula (I) n is an integer from 1 to 5, e.g. 1, 2, 3, 4 or 5. In further preferred fluorous oils of formula (I) m is an integer from 2 to 5, e.g. 2, 3, 4, or 5. In some particularly preferred fluorous oils of formula (I) n and m are identical. In some particularly preferred fluorous oils of formula (I) n is 1 and m is 2. In further preferred fluorous oils of formula (I) p is 0 or an integer from 1 to 5.

In preferred compounds of formula (II), no carbon atoms in the ring are replaced by heteroatoms. Examples of heteroatoms include N, O and S.

In further preferred compounds of formula (II) n is 1 or 2. When n is 1, preferred compounds are those of formula (IIa) wherein g is 1:

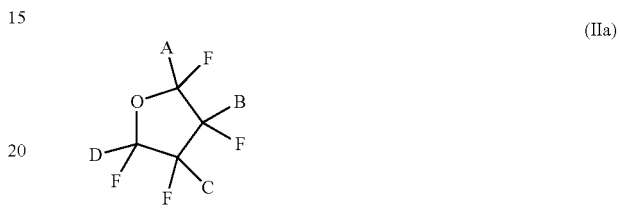

(IIa)

wherein each of A, B, C and D are as defined herein.

In preferred compounds of formula (IIa) D is selected from F and a $C_{1-6}$ fluoroalkyl group. Particularly preferably the fluoroalkyl group is perfluorinated.

When n is 2, preferred compounds are those of formula (IIb):

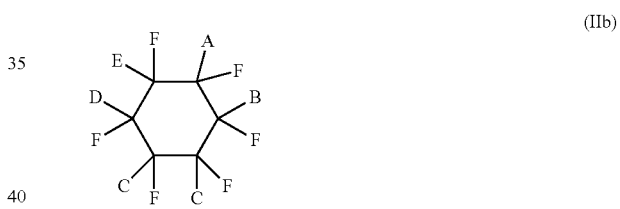

(IIb)

wherein each of A, B, C, D and E are as defined herein.

In preferred compounds of formula (IIb) each of A, B and C are F. In further preferred compounds of formula (IIb), D and E, together with the carbon atoms to which they are attached, form a fluorocycloalkyl ring system. The ring system may be monocyclic or bicyclic. Preferably the fluorocycloalkyl ring system comprises 6 to 14 carbon atoms. Preferably the fluorocycloalkyl ring system is perfluorinated. Particularly preferably the ring system is selected from:

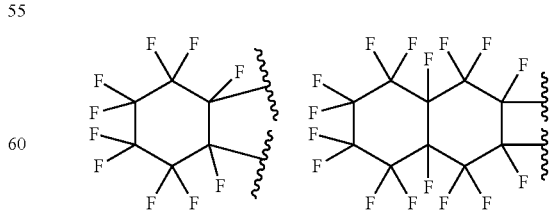

In yet further preferred emulsions of the present invention the fluorous oil comprises at least one compound of formula (Ii)-(Ivi) or formula (IIi)-(IIiv):

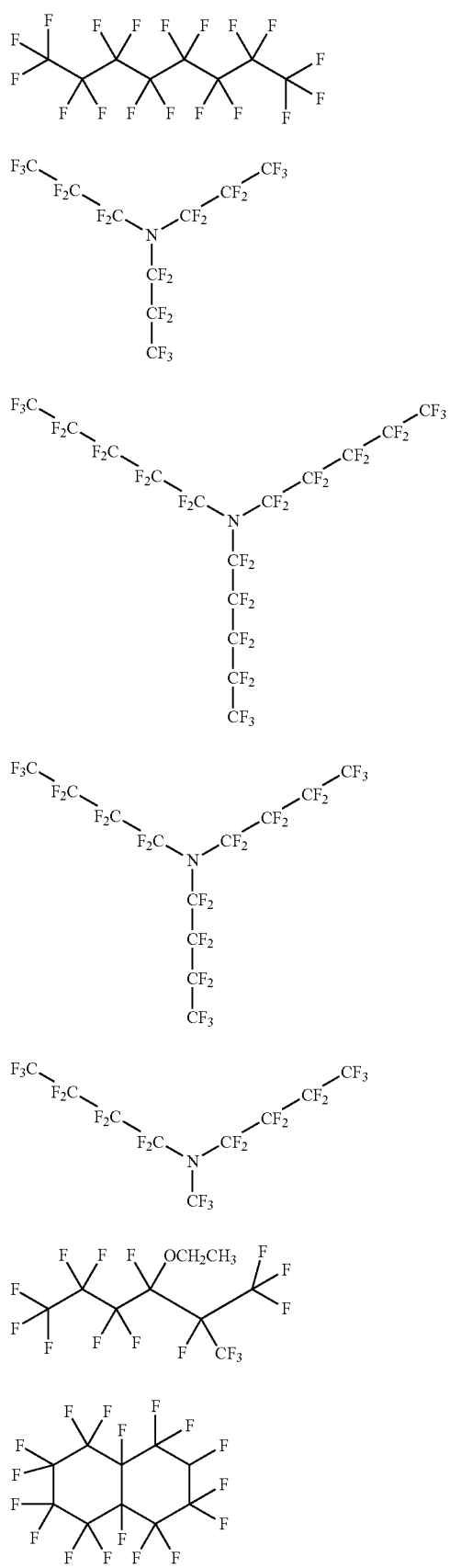
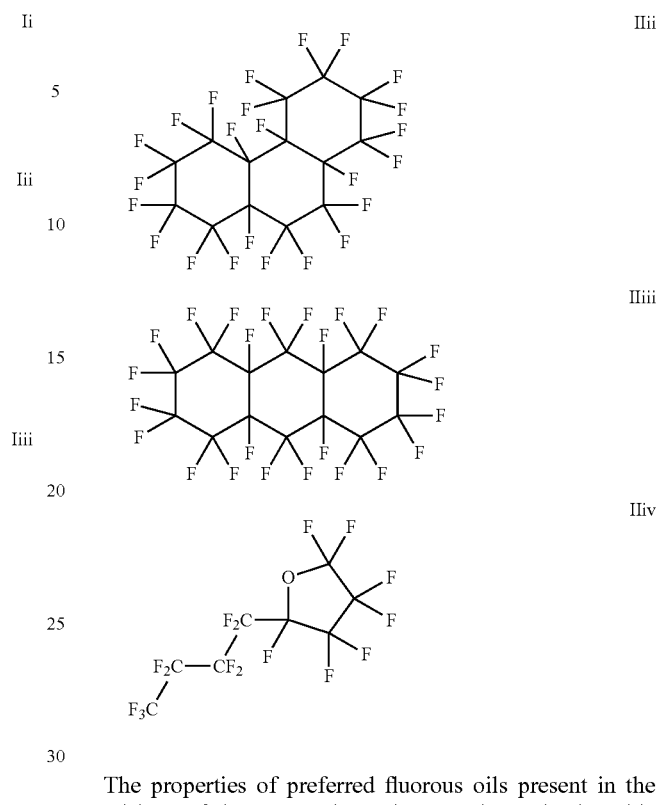

The properties of preferred fluorous oils present in the emulsions of the present invention are shown in the table below.

| Fluorous oil | Refractive Index (RI) | Density (g/ml) | Boiling point (° C.) | LogP |
|---|---|---|---|---|
| (Ii) Perfluorooctane | 1.256 | 1.691 | 102.5 | 6.551 |
| (Iii) 3M Fluorinert FC-3283 | 1.269 | 1.742 | 130 | 15.38 |
| (Iiii) 3M Fluorinert FC-70 | 1.29 | 1.93 | 236 | 16.91 |
| (Iiv) and (Iv) mixture 3M Fluorinert FC-40 | 1.29 | 1.85 | 177 | 19.45 |
| (Ivi) 3M Novec-7500 | 1.287 | 1.56 | 127 | 7.679 |
| (IIi) Perfluorodecalin | 1.3145 | 1.908 | 143 | 7.45 |
| (IIii) Flutec PP11 Perfluorophenanthrene | 1.3315-1.3348 | 2.03 | 212-218 | 10.971 |
| (IIiv) 3M Fluorinert FC-77 | 1.278 | 1.77 | 92-107 | 7.45 |

In especially preferred emulsions the fluorous oil comprises at least one compound of formula (Iiii), (Iiv), (Iv), (Ivi), (IIi) or (IIii). In still more preferred emulsions the fluorous oil comprises at least one compound formula (IIi) or (IIii).

Suitable fluorous oils for use in the emulsions of the present invention are commercially available. Particularly preferably the fluorous oil present in the emulsion is Flutec PP11, shown below.

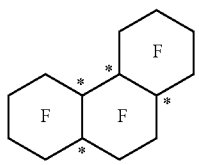

Flutec PP11 is predominantly perfluoroperhydrophenanthrene, which has four chiral carbons (indicated *), giving ten stereoisomers. These are four enantiomeric pairs (RRRS and SSSR; RRSR and SSRS; RRSS and SSRR; RSRS and SRSR) and two meso forms (RRRR; RSSR). In theory, each enantiomeric pair and both meso form may have its own unique physical and chemical properties. In practice, the general inertness of fluorocarbons means that intramolecular effects are negligible, and to all intents and purposes the six forms are identical.

Flutec PP11 also comprises the following compounds as impurities.

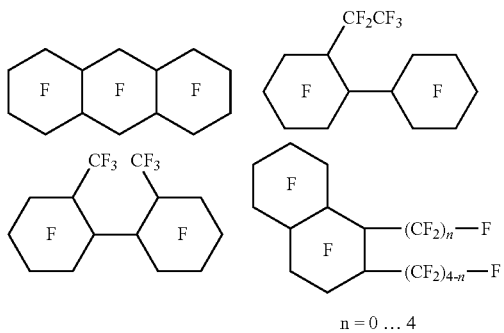

n = 0 ... 4

As described above in the emulsions of the present invention the refractive index of the oil phase (generally also comprising a suitable surfactant to stabilise the emulsion, e.g. Pico-Surf™ 1 and Pico-Surf™ 2 in the region 0.5%-5% by weight) is substantially matched to the refractive index of the aqueous phase by the inclusion of a refractive index modifying compound in the oil phase. Preferably the refractive index modifying compound has a refractive index of greater than 1.333. More preferably the refractive index modifying compound has a refractive index of 1.370 to 1.560, more preferably 1.400 to 1.550, still more preferably 1.420 to 1.550 and yet more preferably 1.500 to 1.545.

Preferably the refractive index modifying compound is soluble in fluorous oil. Preferably the refractive index modifying compound is insoluble in the aqueous phase. Preferably the refractive index modifying compound has a high partition coefficient to enable it to dissolve in a wide range of fluorous oils. Preferably the LogP of the refractive index modifying compound is 1.900 to 8.000, more preferably 3.000 to 8.000 and still more preferably 3.200 to 8.000. Log P valves quoted herein are preferably determined in silico and are from ChemSpider.

Preferably the refractive index modifying compound is liquid at 25° C. Preferably the refractive index modifying compound has no odour. Preferably the refractive index modifying compound has a boiling point of greater than 150° C. More preferably the refractive index modifying compound has a boiling point of 100 to 300° C. and still more preferably 150 to 250° C.

Preferably the density of the refractive index modifying compound is 1.200 to 2.200 g/ml, more preferably 1.300 to 2.000 g/ml and still more preferably 1.400 to 1.990 g/ml.

Preferably the refractive index modifying compound is fluorinated. Particularly preferably the % mass of fluorine in the refractive index modifying compound is greater than 15%. More preferably the % mass of fluorine in the refractive index modifying compound is 15 to 50%, more preferably 16 to 45% and still more preferably 18 to 40%.

In preferred emulsions of the present invention the refractive index modifying compound is a compound of formula (IIIa)

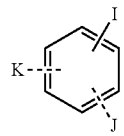

wherein

J and K are optionally present; and each of I, J and K, when present, are independently selected from halogen, a fluoroalkyl group of formula $C_nF_{2n+1}$, OR, $CO_2R$, CONHR, $CONR_2$, CSOR, CSNHR, $CSNR_2$, SR, SOR, $SO_2R$, $SO_3R$, $NHCO_2R$, NHCOR, NHCONHR, $NHCONR_2$, NHCSOR, NHCSR, NHCSNHR, $NHCSNR_2$, NHSOR, $NHSO_2R$ or $NHSO_3R$ wherein n is an integer between 1 and 8, preferably 1 and 6, m is 0, 1 or 2, and R is $C_{1-6}$ alkyl, $C_nF_{2n+1}$ or $(CH_2)_mC_nF_{2n+1}$.

In further preferred refractive index modifying compounds, J is present. Thus preferred compounds are those of formula (IIIb)

(IIIb)

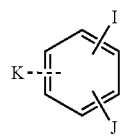

wherein

K is optionally present; and each of I, J and K, when present, are independently selected from halogen, a fluoroalkyl group of formula $C_nF_{2n+1}$, OR, $CO_2R$, CONHR, $CONR_2$, CSOR, CSNHR, $CSNR_2$, SR, SOR, $SO_2R$, $SO_3R$, $NHCO_2R$, NHCOR, NHCONHR, $NHCONR_2$, NHCSOR, NHCSR, NHCSNHR, $NHCSNR_2$, NHSOR, $NHSO_2R$ or $NHSO_3R$ wherein n is an integer between 1 and 8, preferably 1 and 6, m is 0, 1 or 2, and R is $C_{1-6}$ alkyl, $C_nF_{2n+1}$ or $(CH_2)_mC_nF_{2n+1}$.

In some preferred compounds of formula (IIIb) K is absent.

In other preferred refractive index modifying compounds, K is present. Thus preferred compounds are those of formula (IIIc)

(IIIc)

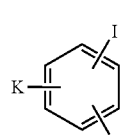

wherein
each of I, J and K are independently selected from halogen, a fluoroalkyl group of formula $C_nF_{2n+1}$, OR, $CO_2R$, CONHR, $CONR_2$, CSOR, CSNHR, $CSNR_2$, SR, SOR, $SO_2R$, $SO_3R$, $NHCO_2R$, NHCOR, NHCONHR, $NHCONR_2$, NHCSOR, NHCSR, NHCSNHR, $NHCSNR_2$, NHSOR, $NHSO_2R$ or $NHSO_3R$ wherein n is an integer between 1 and 8, preferably 1 and 6, m is 0, 1 or 2, and R is $C_{1-6}$ alkyl, $C_nF_{2n+1}$ or $(CH_2)_mC_nF_{2n+1}$.

Compounds of formula (IIIb) and (IIIc) are preferred.

In some preferred compounds of formula (IIIb), I and J are present in positions 1 and 3. In other preferred compounds of formula (IIb), I and J are present in positions 1 and 2. In preferred compounds of formula (IIIc), I, J and K are present in positions 1, 3 and 5 or positions 1, 3 and 4 on the aryl ring.

In further preferred compounds of formula (IIIa), (IIIb) and (IIIc), each of I, J and K, when present, are independently selected from halogen, a fluoroalkyl group of formula $C_nF_{2n+1}$, OR, SR, SOR, $SO_2R$, $SO_3R$, $NHCO_2R$, NHCOR, NHCONHR, $NHCONR_2$, NHCSOR, NHCSR, NHCSNHR, $NHCSNR_2$, NHSOR, $NHSO_2R$ or $NHSO_3R$ wherein n is an integer between 1 and 6, m is 0, 1 or 2, and R is $C_{1-6}$ alkyl, $C_nF_{2n+1}$ or $(CH_2)_mC_nF_{2n+1}$.

In further preferred compounds of formula (IIIa), (IIIb) and (IIIc) I is $CO_2R$, CONHR, $CONR_2$, CSOR, CSNHR, $CSNR_2$, wherein n is an integer between 1 and 8, m is 0, 1 or 2, and R is $C_{1-6}$ alkyl, $C_nF_{2n+1}$ or $(CH_2)_mC_nF_{2n+1}$. Preferably I is $CO_2R$. Preferably R is $(CH_2)_mC_nF_{2n+1}$ wherein m is 1 or 2 and n is an integer between 1 and 8, e.g. 4, 5 or 6. In further preferred compounds of formula (IIIb) and (IIIc), J is also $CO_2R$, CONHR, $CONR_2$, CSOR, CSNHR, $CSNR_2$, wherein n is an integer between 1 and 8, m is 0, 1 or 2, and R is $C_{1-6}$ alkyl, $C_nF_{2n+1}$ or $(CH_2)_mC_nF_{2n+1}$. Preferably J is $CO_2R$. Preferably R is $(CH_2)_mC_nF_{2n+1}$ wherein m is 1 or 2 and n is an integer between 1 and 8, e.g. 4, 5 or 6. In such compounds K is preferably absent.

In further preferred compounds of formula (IIIa), (IIIb) and (IIIc), I is a fluoroalkyl group of formula $C_nF_{2n+1}$, wherein n is an integer between 1 and 6. Preferably n is 1 to 3, especially 1, i.e. I is $CF_3$. In further preferred compounds of formula (IIIb) and (IIIc), J is a halogen or a fluoroalkyl group of formula $C_nF_{2n+1}$, wherein n is an integer between 1 and 6. Preferably n is 1 to 3, especially 1, i.e. J is $CF_3$. Particularly preferably J is halogen, e.g. Br, Cl or I.

In further preferred compounds of formula (IIIc), K is halogen, OR, SR, SOR, $SO_2R$, $SO_3R$, $NHCO_2R$, NHCOR, NHCONHR, $NHCONR_2$, NHCSOR, NHCSR, NHCSNHR, $NHCSNR_2$, NHSOR, $NHSO_2R$ or $NHSO_3R$, wherein n is an integer between 1 and 6, m is 0, 1 or 2, and R is $C_{1-6}$ alkyl, $C_nF_{2n+1}$ or $(CH_2)_mC_nF_{2n+1}$. Preferably R is $C_{1-3}$ alkyl, especially $CH_3$. Particularly preferred compounds of formula (IIIc) are those wherein K is halogen (e.g. Br, Cl or I), $NHCO_2R$ or NHCSOR wherein R is $C_{1-3}$ alkyl, especially $CH_3$, or $(CH_2)_mC_nF_{2n+1}$ where m is 0, 1 or 2 and n is an integer from 1 to 6. Still further preferred compounds of formula (IIIc) are those wherein K is halogen, e.g. Br, Cl or I.

Particularly preferably the compound of formula (IIIa) is selected from:

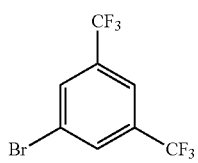
a

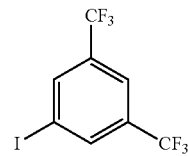
b

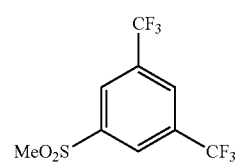
c

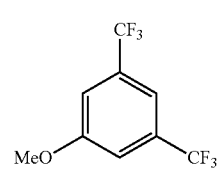
d

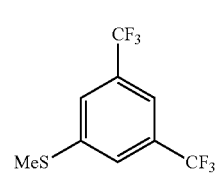
e

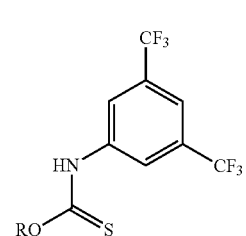
f where R is $(CH_2)mCnF2n+1$,
m is 0, 1 or 2
n is an integer from 1 to 8.

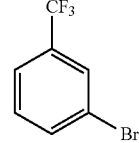
g

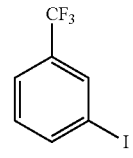
h

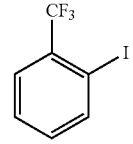
i

-continued
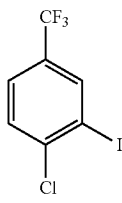
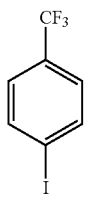
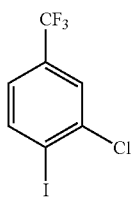
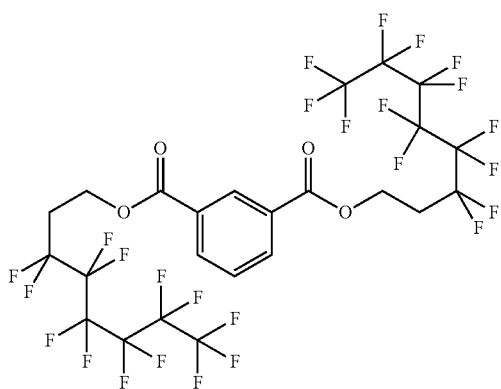
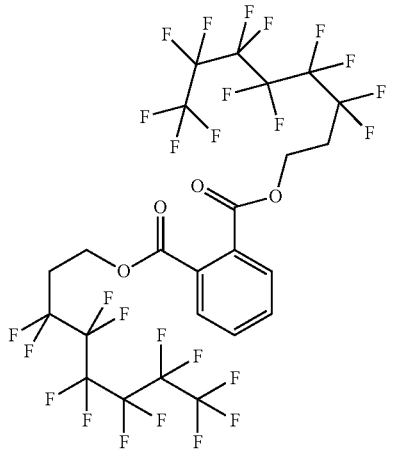
Especially preferably the compound of formula (IIIa) is:
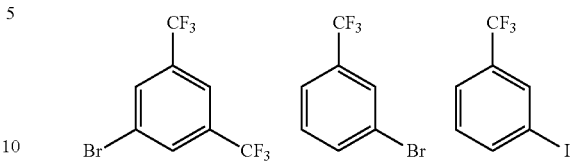
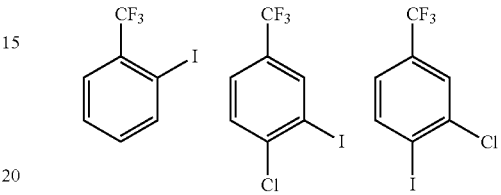
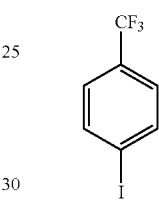
Especially preferably the compound is a compound of formula (IIIa) is:
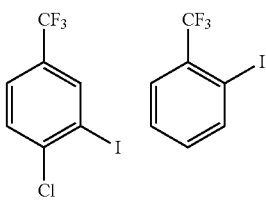
Two other preferred compound of formula (IIIa) are:
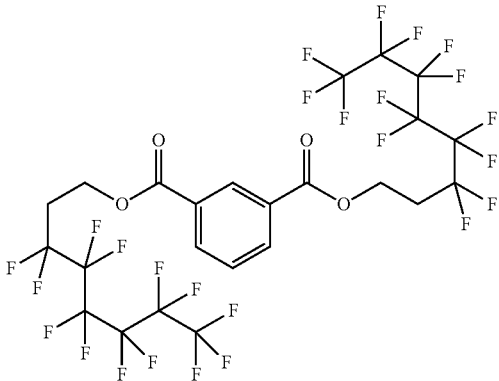

-continued
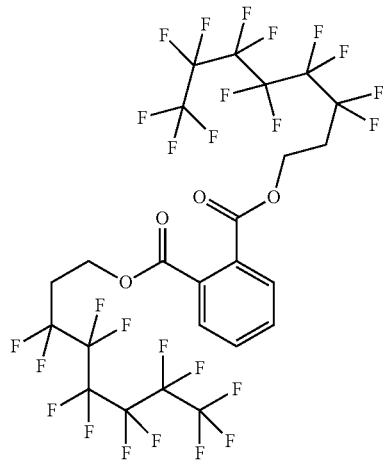
The properties of preferred refractive index modifying compounds are shown in the table below.
| Refractive index modifying compound | Refractive Index (RI) | Density (g/ml) | Boiling point (° C.) | LogP | % mass of F |
|---|---|---|---|---|---|
| a (3,5-bis(CF₃), Br) | 1.427 | 1.698 | 154 | 3.444 | 39 |
| b (3,5-bis(CF₃), I) | 1.462 | 1.904 | 184 | 5.07 | 34 |
| c (3,5-bis(CF₃), MeO₂S) | 1.42 | 1.474 | 285 | 1.935 | 39 |
| d (3,5-bis(CF₃), MeO) | 1.391 | 1.352 | 158 | 3.433 | 44 |
| e (3,5-bis(CF₃), MeS) | 1.448 | 1.41 | 178 | 4.367 | 44 |
| g (3-CF₃, Br) | 1.473 | 1.617 | 151 | 3.36 | 25 |
| h (3-CF₃, I) | 1.517 | 1.887 | 82 @ 25 mmHg | 3.898 | 21 |
| i (2-CF₃, I) | 1.54 | 1.952 | 58 @ 0.5 mmHg | 4.85 | 19 |
| j (CF₃, Cl, I) | 1.534 | 1.98 | 58 @ 0.2 mmHg | 5.271 | 19 |
| k (4-CF₃, I) | 1.531 | 1.939 | 197 @ 750 mmHg | 4.253 | 21 |
| l (CF₃, Cl, I) | 1.516 | 1.851 | 185 @ 745 mmHg | 3.87 | 21 |

Some refractive index modifying compounds are commercially available. Others may be prepared by conventional synthetic organic chemistry.

Certain compounds of formula (IIIb) are believed to be novel. Thus in a further aspect the present invention provides a compound of formula (IV)

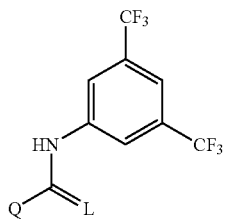

(IV)

wherein
L is S or O; and
Q is NHR, NR$_2$ or OR, wherein R is C$_{1-6}$ alkyl or (CH$_2$)$_m$(CF$_{2p+1}$)$_p$,
m is 0, 1 or 2; and
p is an integer between 1 and 6.

Preferably L is S. Preferably R is (CH$_2$)$_m$(CF$_{2p+1}$)$_p$. When p is 1, R is (CH$_2$)$_m$CF$_3$ and when p is 2, R is (CH$_2$)$_m$C$_2$F$_5$ and so on. Alternatively expressed, R is preferably (CH$_2$)$_m$C$_n$F$_{2n+1}$ wherein m is 0, 1 or 2 and n is an integer between 1 and 6.

In a further related aspect the present invention provides a process for making a compound of formula (IV) comprising reacting a compound of formula (V)

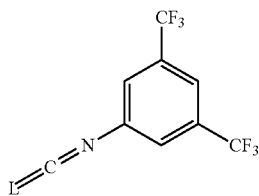

(V)

wherein L is S or O with a compound of formula ROH, RNH$_2$ or R$_2$NH, wherein R is C$_{1-6}$ alkyl or (CH$_2$)$_m$(CF$_{2p+1}$)$_p$, m is 0, 1 or 2, and p is an integer between 1 and 6.

In a yet further aspect the invention provides a compound of formula (VI):

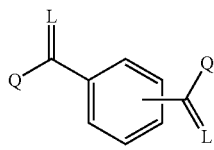

(VI)

wherein
L is O or S;
Q is OR, NHR or NR$_2$, wherein R is C$_{1-6}$ alkyl or (CH$_2$)$_m$(CF$_{2p+1}$)$_p$;
m is 0, 1 or 2; and
p is an integer between 1 and 8.

Preferably L is O. Preferably Q is OR. Preferably R is (CH$_2$)$_m$(CF$_{2p+1}$)$_p$. When p is 1, R is (CH$_2$)$_m$CF$_3$ and when p is 2, R is (CH$_2$)$_m$C$_2$F$_5$ and so on. Alternatively expressed, R is preferably (CH$_2$)$_m$C$_n$F$_{2n+1}$ wherein m is 0, 1 or 2 and n is an integer between 1 and 8.

In a further related aspect the present invention provides a process for making a compound of formula (VI) comprising reacting a compound of formula (VII)

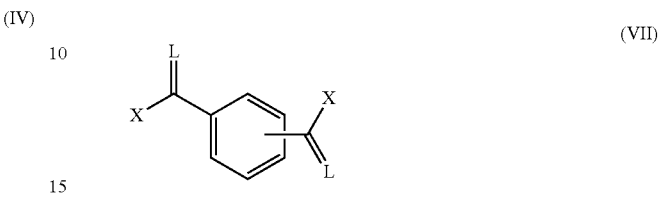

(VII)

wherein L is O or S and X is a leaving group, e.g. halide, with a compound of formula ROH, RNH$_2$ or R$_2$NH, wherein R is C$_{1-6}$ alkyl or (CH$_2$)$_m$(CF$_{2p+1}$)$_p$, m is 0, 1 or 2, and p is an integer between 1 and 8.

In preferred emulsions of the present invention the % wt of fluorous oil in said oil phase is 75 to 99% wt, more preferably 90 to 99% wt and still more preferably 95 to 99% wt. Correspondingly the % wt of refractive index modifying compound in said oil phase is 0-25% wt, more preferably 0 to 10% wt and still more preferably 0 to 5% wt.

In preferred emulsions of the present invention the aqueous phase in the emulsion is in the form of droplets. Preferably the droplets have an average diameter of 5 to 120 µm, more preferably 5 to 110 µm and still more preferably 5 to 80 µm. Preferably each discontinuous aqueous phase (e.g. droplet) comprises an average number of 0 to 100 analytes, more preferably 1 to 20 and still more preferably 1 to 5, e.g. 1 analyte. The analyte is preferably a bead, a particle, a crystal, a micelle, a macromolecule (e.g. a protein or an oligonucleotide), a cell (e.g. mammalian cell, plant cell, algal cell, yeast cell), cell organelles (e.g. cell nucleus, mitochondrion), a bacterium, a virus or a prion. More preferably the analyte is a cell, a bacterium, a virus, a prion or a macromolecule (e.g. a protein or an oligonucleotide). Still more preferably the analyte is a cell When the aqueous phase comprises a living entity, e.g. cell or bacterium, the aqueous phase preferably comprises a culture or growth medium. Any conventional medium may be used. The medium may, for example, comprise glucose, vitamins, amino acids, proteins, salts, pH indicators and density matching reagents, e.g. Ficoll. In many cases the medium may also comprise coloured or fluorescent compounds which would interfere with the reliability of many conventional optical assays. The presence of such compounds does not, however, impact on the reliability of the methods of the present invention.

Typically the presence of the culture or growth medium in the aqueous phase increases its refractive index. Sufficient medium must be provided to keep the entity alive for the duration of the analysis including sorting in the microfluidic device. Preferably therefore the aqueous phase comprises 90 to 99% wt water and more preferably 95 to 99% wt water.

The emulsion may comprise oil phase and aqueous phase in any amounts suitable to form an emulsion. The skilled man will readily be able to determine such amounts.

Preferred emulsions of the invention further comprise a surfactant and preferably a fluorosurfactant. Preferably the amount of surfactant is 0.5 to 5% wt based on the total weight of the emulsion. Generally the amount of surfactant present in the emulsion is so low that it does not significantly impact on the refractive index of the oil phase. Preferably the fluorosurfactant is Pico-Surf™ 1 and Pico-Surf™ 2 which are commercially available.

In a further aspect the present invention relates to a kit for preparing an oil having a refractive index that substantially matches the refractive index of an aqueous mixture comprising:

(i) a first container comprising a first fluorous oil and optionally a surfactant;

(ii) a second container comprising a first refractive index modifying compound comprising at least one aromatic ring and optionally a surfactant;

(iii) optionally a third container comprising a surfactant; and (iv) instructions to prepare a series of oils having a constant surfactant concentration but different refractive indexes by mixing said fluorous oil and said refractive index modifying compound in different proportions and to mix each of said resulting oils with said aqueous mixture to identify an oil having a refractive index that substantially matches the refractive index of the aqueous mixture.

Preferred kits of the invention comprise a surfactant. In some preferred kits the first container consists of a first fluorous oil and the second container consists of a first refractive index modifying compound. In this case, the kit preferably comprises a third container comprising a surfactant. The surfactant can then be added during preparation of the series of oils. Preferably the concentration of surfactant is constant across the series of oils. In other preferred kits of the invention the first container and/or second container comprise a surfactant. Again the concentration of surfactant in the final series of oils is preferably constant.

Preferably the instructions to identify oil having a refractive index that substantially matches the refractive index of the aqueous mixture describe visually analysing the emulsion comprising oil phase and aqueous phase to assess the level of refractive index matching. The less distinguishable the two phases are to the eye, the closer the refractive index matching. Alternatively the refractive index of the oil phase and/or the aqueous mixture can be measured, e.g. with a refractometer and compared.

Preferred features of the kit are the same as those preferred features of the emulsion described above. Thus preferred fluorous oils, refractive index modifying compounds and surfactants present in the kit are those described above in relation to the emulsion.

Particularly preferred kits of the present invention further comprise a second fluorous oil. Some preferred kits of the invention comprise a fourth container comprising the second fluorous oil. In other preferred kits the second fluorous oil is present in the second container comprising the refractive index modifying compound. When two oils are provided the first fluorous oil is preferably perfluorodecalin (IIi) and the second fluorous oil is preferably perfluorophenanthrene (IIii).

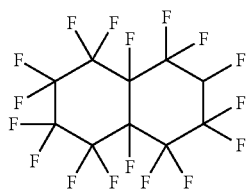

IIi

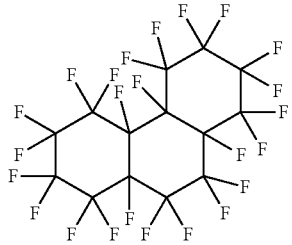

IIii

A particularly preferred kit of the present invention comprises:

(i) a first container comprising a first fluorous oil and a surfactant;

(ii) a second container comprising a second fluorous oil, a first refractive index modifying compound comprising at least one aromatic ring and a surfactant; and (iii) instructions as set out above.

Further preferred kits of the present invention comprise a second refractive index modifying compound comprising at least one aromatic ring. Some kits further comprise a fifth container comprising the second refractive index modifying compound. In other kits, the first container comprising a first fluorous oil and/or a fourth container comprising a second fluorus oil additionally comprises a second refractive index modifying compound.

A particularly preferred kit of the present invention comprises:

(i) a first container comprising a first fluorous oil, a second refractive index modifying compound and a surfactant;

(ii) a second container comprising a second fluorous oil, a first refractive index modifying compound comprising at least one aromatic ring and a surfactant; and (iii) instructions as set out above.

In the above kits, the amount of surfactant present in the various containers is preferably constant. This enables oils comprising a constant amount of surfactant with varying amounts of fluorous oils and/or refractive index modifying compound, and therefore varying refractive indices, to be prepared.

Yet further preferred kits of the invention comprise a series of containers, each comprising a different refractive index modifying compound as described herein. The kits of the present invention may optionally comprise a series of containers for mixing a fluorous oil and a refractive index modifying compound.

In a further aspect the present invention also relates to a method of preparing an emulsion as hereinbefore described comprising:

(i) preparing an aqueous mixture comprising at least one analyte; (ii) preparing an oil comprising a fluorous oil and a refractive index modifying compound comprising at least one aromatic ring; and (iii) mixing the aqueous mixture and the oil to form an emulsion, wherein the refractive index of the aqueous phase and the refractive index of the oil phase are substantially matched.

For testing the refractive index matching of an aqueous solution and a fluorous oil, a small volume of each solution may be placed in a clear vial and vortexed. The vortexing yields an emulsion that is highly disperse. The upper phase of the emulsion can, however, be visually checked for its degree of transparency compared to the bottom fluorous oil phase. The less well matched the refractive indices of the two phases are the more opaque the upper emulsion will appear.

In preferred methods of the present invention the mixing is by a flow focus junction of a microfluidic device.

Further preferred features of the method of preparing an emulsion are the same as the preferred features of the emulsion described above. Thus preferably the emulsion, the aqueous mixture/phase and the oil are as defined above in relation to the emulsion.

In a further aspect the present invention also relates to a method for sorting droplets in a microfluidic device, the method comprising:

(i) providing a stream of droplets in an emulsion as defined herein in a channel of the microfluidic device;

(ii) illuminating said stream from a first direction;

(iii) detecting light from analytes within the droplets in a second direction; and (iv) sorting the droplets into one of a plurality of differentiated streams responsive to said detected light.

In preferred methods the illuminating comprises illuminating using a fibre optic to illuminate substantially the whole of the channel, i.e. the entire cross-section of a droplet. Preferably the light from the analytes and optionally the droplet interface and fluorescent markers, is detected. Preferably detection of light is from the whole of the channel, i.e. substantially the entire cross-section of a droplet. Detection may be by the same optical fibre as illumination or by a detector at an angle to the incident illumination source.

Thus in some methods the first direction is different to the second direction, but in other embodiments of the method the first and second directions may be the same (more specifically, anti-parallel): potentially, collecting the light down the fibre can be more sensitive. In particular when looking for cell surface markers, for example using fluorescently-labelled antibodies, then one may deliver the laser excitation light via the fibre and collect the fluorescence also back down the same fibre. The advantage of the refractive index matching in this example is that removing the boundary interface increases the magnitude of the fluorescence signal observed from the cell's surface, by reducing "lasing" in the cell and other effects resulting from light being reflected around within the droplet.

Techniques of this type can, for example, be useful in detecting specific types of cell possessing a specific cell surface marker, e.g. a cancer cell, stem cell or in differentiating between normal cell types. Furthermore if, say, an antibody binds to a cell surface protein (antigen) and modifies the functional behaviour of this protein (i.e. the antibody acts as an agonist, a partial agonist, an antagonist or a partial antagonist), this may be monitored by a fluorescence assay, either within the cell, or if external to the cell within the droplet. Again, by refractive index matching the fluorous oil to the aqueous droplet then the ability to detect the fluorescence signal either from within the cell, or at the surface of the cell, or in the volume of the droplet is improved, together with the magnitude of the observed signal.

Although, as described above, in general the analytes comprise or interact with cells, in principle the techniques we describe may also be employed in other contexts.

Thus the aspects/embodiments of the invention described herein also contemplate replacing the cells with other analytes such as proteins or other molecules. For example embodiments of the methods we describe in principle facilitate detection of one or more of molecular aggregation, mass changes, and agglutination, in particular because of a change (increase/decrease) in entity size and thus a related change in light scattering power.

Particularly preferred methods further comprise determining a number of analytes in each droplet from said scattered light. In yet more preferred methods, sorting of the droplets into one of a plurality of differentiated streams is responsive to the determined number. Preferably determining comprises determining an integrated intensity of the scattered light over time and determining at least whether said number of analytes falls above or below a threshold.

Further preferred features of the method of sorting are the same as the preferred features of the emulsion described above. Thus preferably the emulsion, the aqueous phase and the oil phase are as defined above in relation to the emulsion.

BRIEF DESCRIPTION OF THE DRAWINGS

These and other aspects of the invention will now be further described, by way of example only, with reference to the accompanying figures in which:

FIGS. 3*a* and 3*b* show a system for label-free cell sorting in a microfluidic device according to an embodiment of the invention;

DETAILED DESCRIPTION OF PREFERRED EMBODIMENTS

It is difficult to detect particles (e.g. cells) encapsulated in surfactant stabilised water in fluorous microdroplets due to the relatively large amount of light scattering produced from the droplet interface. This light scattering at the droplet interface is due to reflection of light at the interface caused by a difference in refractive index of the two liquids.

Figure 1:
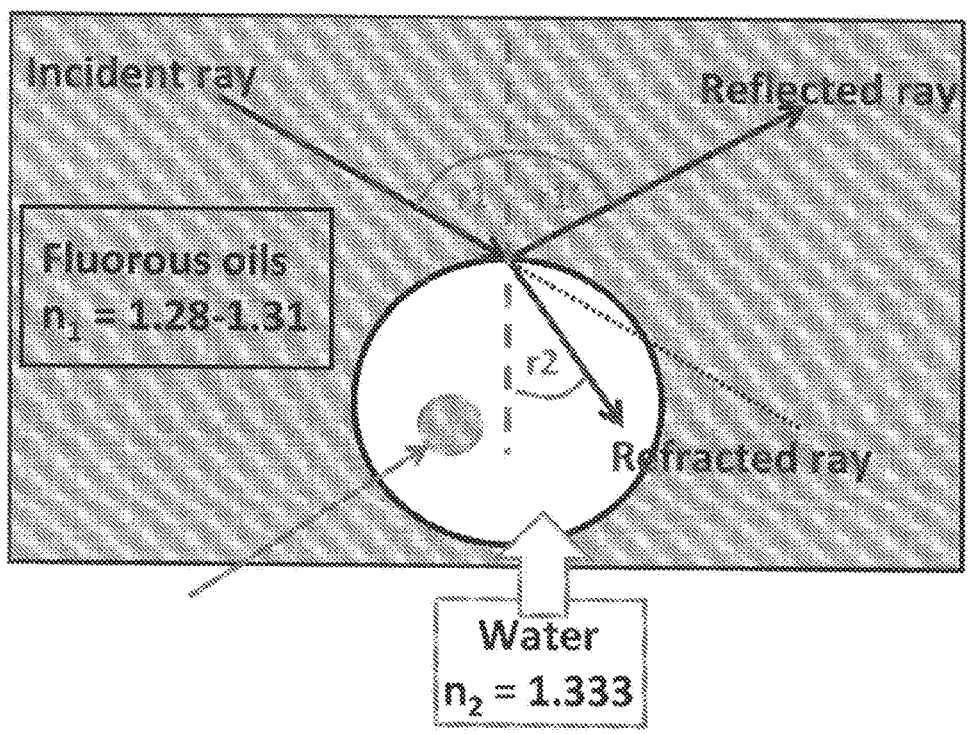
FIG. 1 shows, schematically, scattering from a microdroplet of an emulsion.

Referring to FIG. 1*a*, this shows a water droplet in (fluorous) oil. A reflected ray lies in the plane of incidence and has an angle of reflection ($r'_1$) equal to the angle of incidence ($r_1$). Snell's law relates the angle of incidence of light with the angle of the refracted ray ($r_2$) at the boundary between two isotropic media:

$$n_2 \sin r_2 = n_1 \sin r_1$$

where $n_1$ and $n_2$ are the respective refractive indices (RI) of, here, the oil and water respectively. Typically $n_2 = 1.333$ (but this may be modified by the presence of growth medium in the water) and for a typical fluorous oil $n_1$ is in the range 1.28-1.3348. The relatively large amount of light scattered as a result of the droplet interface masks the presence of a small particle or cell in a droplet, which produces a relatively small amount of light scattering.

Nonetheless, surprisingly the inventors have established that if the scattering at the boundary of the droplet is suppressed (by refractive index matching) it is possible to detect individual cells within a droplet, and sort droplets within a stream of emulsion on this basis. This enables a label-free approach to active dielectrophoretic cell sorting in a microfluidic device.

Figure 2:
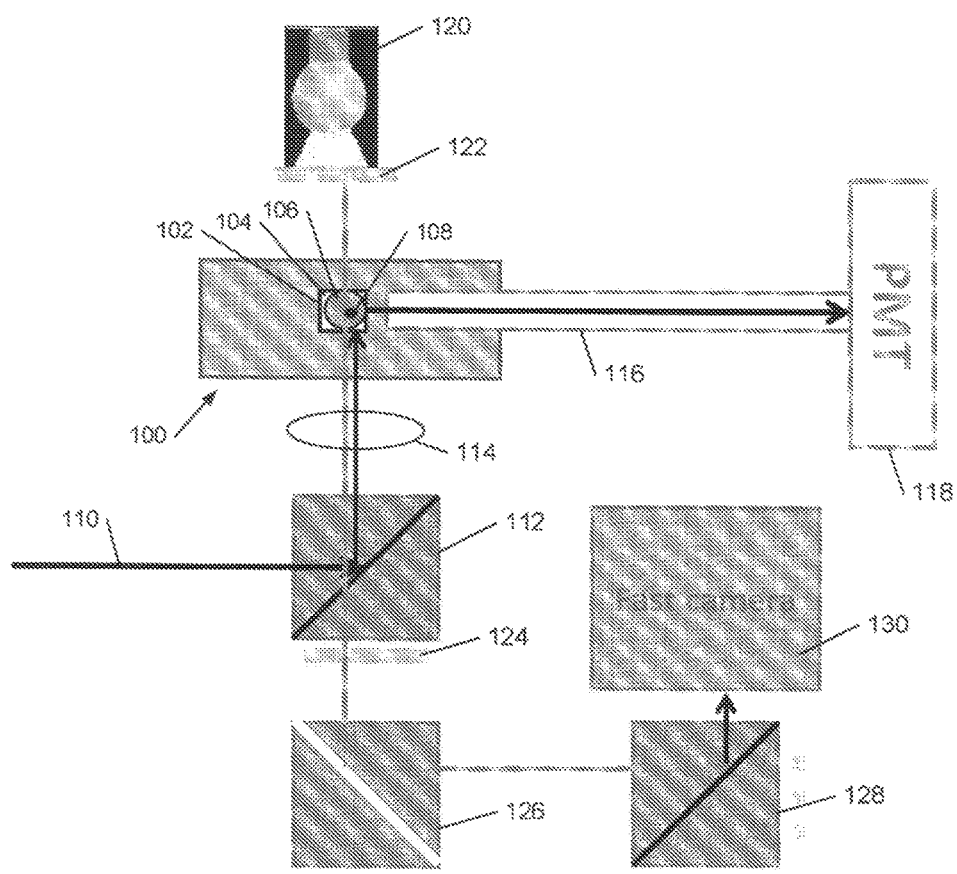
FIG. 2 shows an experimental arrangement for detection of cells within microdroplets according to an embodiment of the invention.

FIG. 2 illustrates experimental apparatus for visualising cells within droplets. The apparatus comprises a microfluidic device [100], shown in cross-section, having a channel [102] in which flows a stream of emulsion [104] comprising aqueous droplets [106] within fluorous oil, at least some of the droplets containing one or more cells [108] in the illustrated arrangement the channel is illuminated by a beam [110] from a laser (not shown) via a beam splitter [112] and lens [114]. In one experimental arrangement a 24.5 mW 594 nm laser was employed. In the illustrated arrangement side-scattered light is collected by a fibre optic [116] embedded in the microfluidic device, in one experiment a 105 µm fibre, and provided to a photomultiplier tube (PMT) [118] which responds to scattered light from the cells. In addition in this experimental apparatus a white light illumination source [120] illuminated the channel from above (via a band-pass filter [122]) and the channel was viewed from beneath via beam splitter [112], a long-pass filter [124] and mirrors (beam splitters) [126], [128], by a fast video camera [130]. In the arrangement of FIG. 2 one wavelength is employed to view the droplets and a second to count cells.

FIG. 3a shows details of the microfluidic device [100], and FIG. 3b an alternative arrangement for the detection of scattered light viewing back-scattered rather than side-scattered light. Thus referring to FIG. 3a the device [100] has a first inlet port [150] for the (fluorous) oil and a second inlet port [152] for the aqueous mixture, the oil flowing in to opposite sides of a channel [154] to form a flow-focused junction [156] having an output channel [158] carrying a water-in-oil emulsion.

The aqueous medium provided to port [152] includes cells at a concentration which may be varied according to the desired number of cells per droplet. In some applications the average number of cells per droplet may be less than one so that few droplets have more than one cell; in other applications a few tens or potentially hundreds of cells may be present in each droplet.

The emulsion is provided to a cell sorting region [160] comprising a pair of electrodes [162a, b] adjacent a Y-junction with output and waste channels 164, 166. By default the droplets progress to waste channel [166] but application of a voltage cross electrode [162] distorts the droplet directing it into output channel [164]. The voltage applied to electrodes [162] is controlled by a controller (not shown) in response to the detection of scattered light from cell or cells within a droplet, as explained further later. The optical fibre [116] is used to illuminate and/or view the scattered light from cells within the droplets. In one example the device of FIG. 3a comprised a 50° sorting chip with a 54 µm by 54 µm by 75 µm flow focus droplet generator, having a waste channel width of 142 µm. The skilled person will appreciate, however, that the arrangement of FIG. 3a illustrates proof-of-principle apparatus and that many other more complex arrangements are possible and may be employed for particular applications.

FIG. 3b illustrates an expanded view of region X of FIG. 3a illustrating an alternative cell detection arrangement to that of FIG. 2. In this arrangement the optical fibre [116] is used for both illumination of the channel and detection of the back-scattered light. As illustrated, illumination is by a 488 nm laser via a beam splitter [170] with respective first and second fibre optic ports [172a, b] to couple to fibre [116] and the laser input, and to provide an output to detector [174]. In one embodiment beam splitter [170] was a 50:50 beam splitter and detector [174] was a PDA 36A amplified silicon detector having a useful response over the wavelengths range 400-1100 nm. The skilled person will appreciate that the laser wavelength and power may be varied according to the application—for example the refractive indices of the (modified) oil and aqueous medium both vary with wavelength and thus the degree of matching may be adjusted by selecting the wavelength of operation of the system. For some applications the best possible match may be desired; for others a slight mismatch may be desirable to facilitate the detection/visualisation of the droplets as well as their contents. The laser power may be selected by routine experiment—broadly speaking larger powers make it easier to detect the scattered light although unwanted side-effects or additional scattering may occur with high laser powers and, more generally, lower powers are desirable for eye safety. For similar reasons wavelengths longer than 1000 nm may also be desirable to facilitate achieving eye safety. Conveniently in embodiments a telecoms class 1 fibre coupled laser diode may be employed, for example at a wavelength in the range 1310 nm-1610 nm, such as 1550 nm, with a power of less than, for example, 5 mW.

Figure 4:
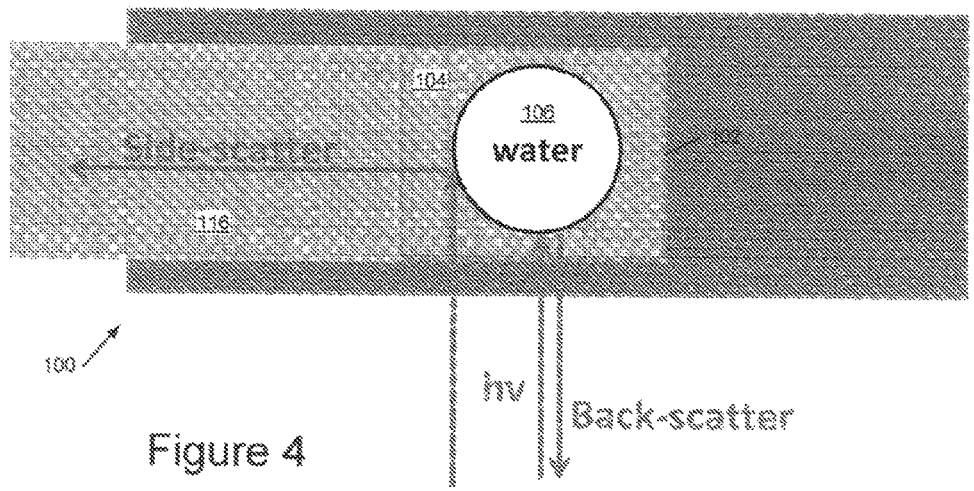
FIG. 4 shows a configuration of an optical fibre for the system of FIG. 3.

FIG. 4 schematically illustrates back-scattering and side-scattering techniques which may be employed. It is helpful to provide good optical coupling of the fibre [116] to the channel [102] and one approach which has been found useful is to push the fibre into a channel of the microfluidic device containing soft/unpolymerised material (for example PDMS) with a side chamber at the end for the trapped air. After insertion of the fibre to the end wall of the channel and expulsion of the air, the chip is carefully placed in an oven at 110° C. for approximately 1 hour to polymerise the polymer around the fibre in the channel.

Figure 5:
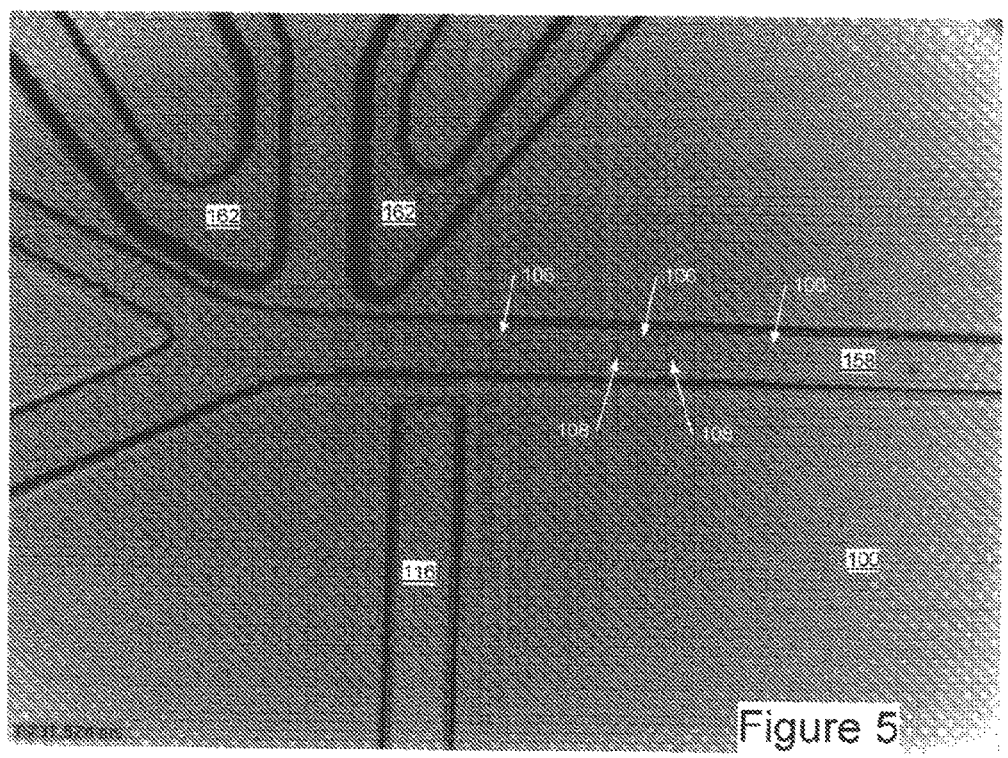
FIG. 5 illustrates microdroplets in the device of FIG. 3 with partial index matching.

FIG. 5 shows a captured image of microdroplets [106] within the device of FIG. 3a, some of the droplets containing cells [108]. The image illustrates an emulsion with a deliberately partially mismatched oil-droplet refractive index.

Figure 6:
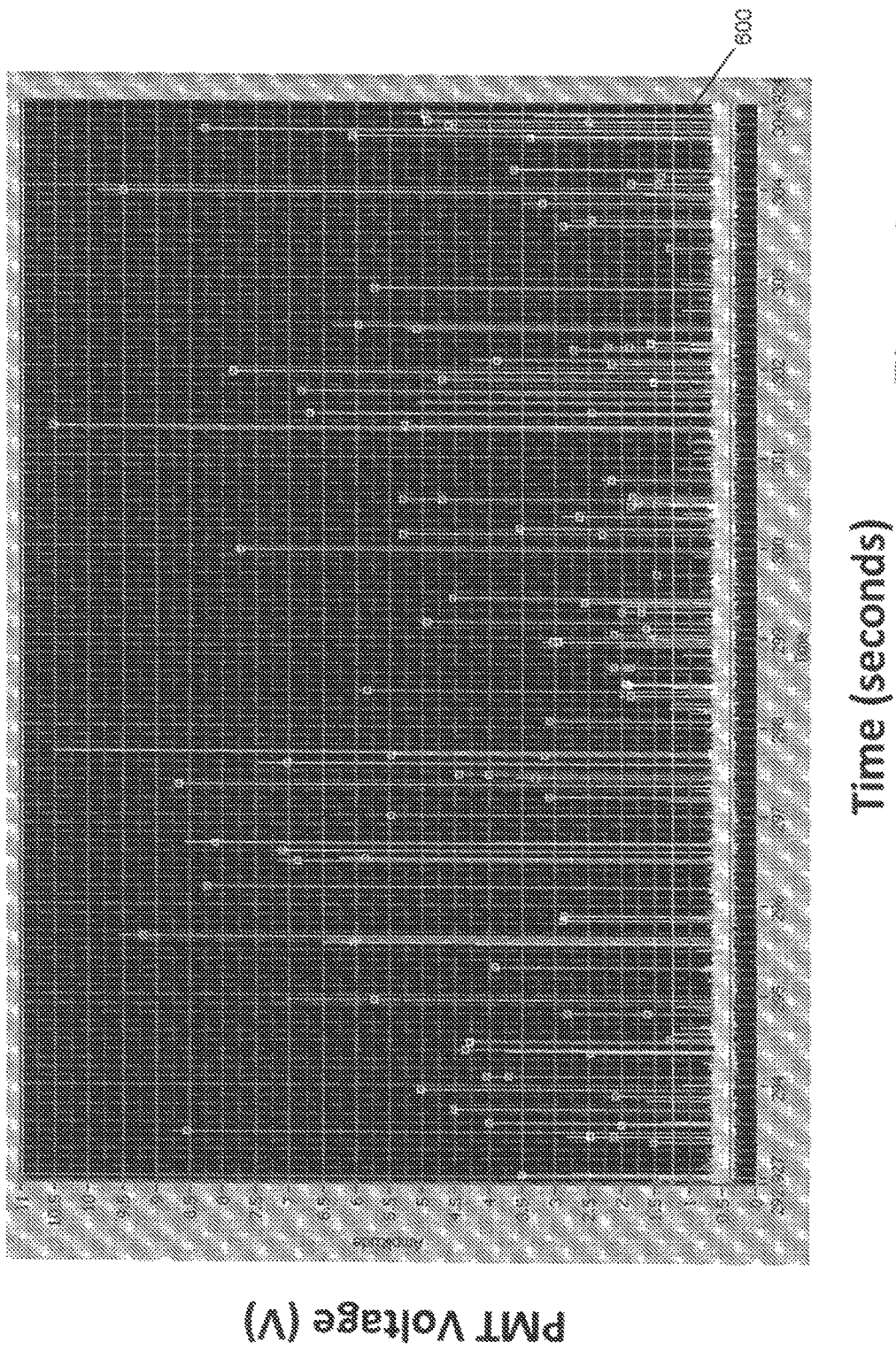
FIG. 6 illustrates the signal from a detector in the system of FIG. 3 illustrating peaks from scattered light from cells within droplets, for implementing a method of sorting according to an embodiment of the invention.

FIG. 6 illustrates a signal from photomultiplier [118] of FIG. 2. Each of the peaks corresponds to detection of one or more cells within a microdroplet. A base line [600] may be established above which detection of a cell or cells is deemed to have taken place.

Figure 7:
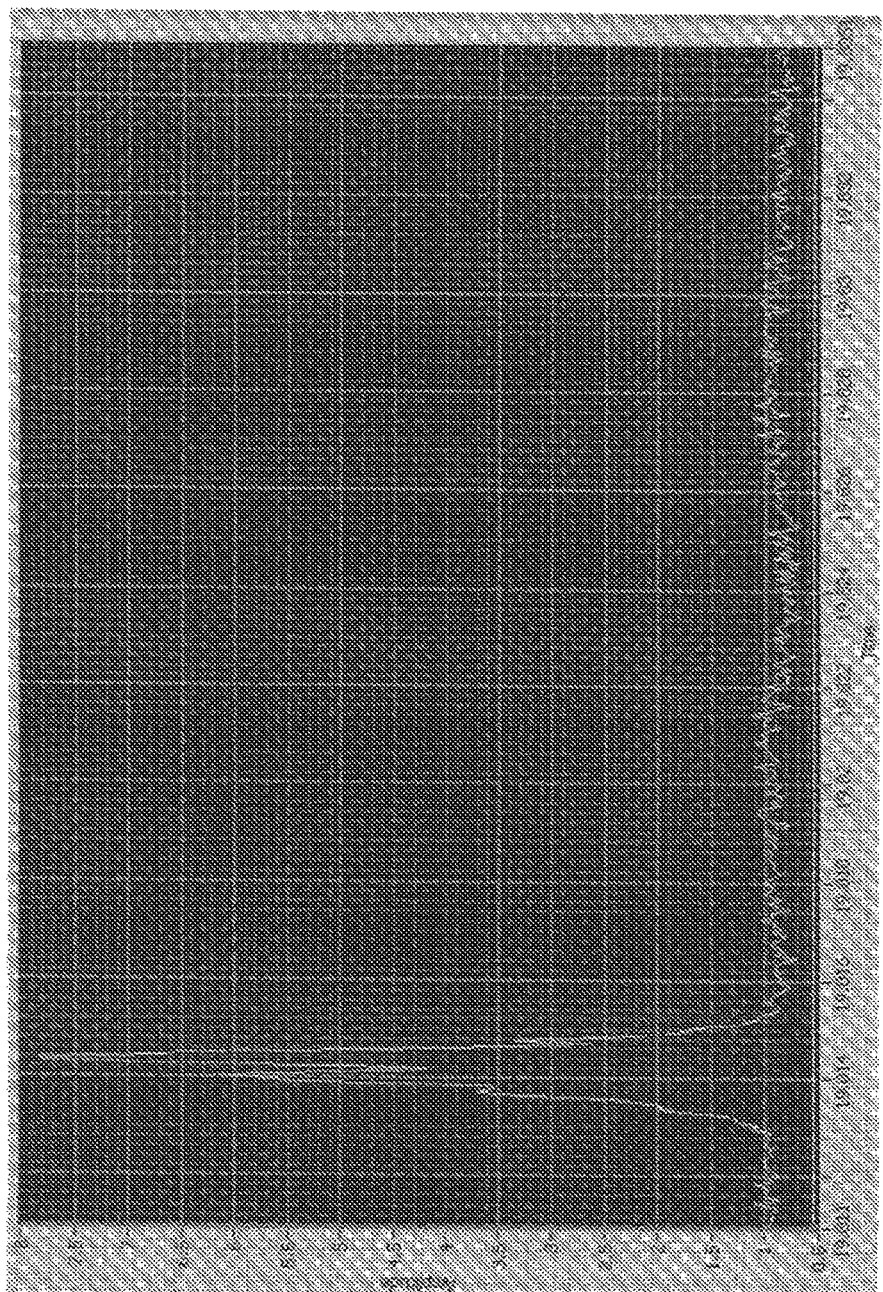
FIG. 7 illustrates a peak of FIG. 6 on an expanded timescale.

FIG. 7 illustrates a single peak on an expanded scale. As can be seen, when magnified, the peak is not "clean" in that multiple sub-peaks can be discerned. Experimentally the area under the curve can be correlated with the number of cells within a droplet; the area may be taken to be that above a base line for the system. The duration of a peak, for example measured by time above a threshold level such as the base line, also correlates with the number of cells in a droplet; as does the peak height, albeit to a lesser extent. Thus one or more of these measures may be employed to determine a count or a range for a number of cells in a droplet or in other applications, whether the number of cells is greater or less than a threshold for sorting.

One application for the above described techniques is a proliferation assay. In one example of such an assay 112 μm diameter (740 femtoliter volume) droplets each comprising of order 20 bacteria are generated at a rate of 70 kHz. The droplets include antibiotic; most of the bacteria are deactivated by the antibiotic but a small proportion of the population is resistant and proliferates. The bacteria are maintained within the droplets for sufficient time to allow proliferation and sufficient bacteria, for example, of order one billion, are processed to allow the antibiotic resistant phenotype to be extracted. Such a proliferation assay may be performed by counting cells within the droplets as previously described. The label-free approach enables the use of small droplets and a high throughput rate thus making such an approach practical. The skilled person will recognise that, nonetheless, embodiments of the technique may also be employed in conjunction with fluorescence labelling such as FRET, chromatic vesicles or particles, cell surface markers, functional assays and cell viability dyes.

More particularly, embodiments of the techniques can be employed to reduce the risk of fluorescence light (generated either from a cell or particle, or even from a homogeneous fluorescence assay within a microdroplet) being trapped within a droplet by internally reflection. Thus embodiments of the techniques benefit fluorescence monitoring, as described further below:

Consider, in a first example, an antibody producing cell generates an antibody that binds to a protein located on the surface of a second cell. In this case the binding event may be observed by a second fluorescently-labelled antibody that binds to a region of the first antibody (in an area not associated to its variable binding region). In this case we can use the techniques we describe to to discriminate a highly fluorescent particle from a low background fluorescence homogeneously dispersed throughout the droplet.

Consider, in a second example, an antibody producing cell produces an antibody that binds to a protein located on the surface of a second cell, and in which the binding of the antibody to the protein on the cell surface has a functional effect on the protein (e.g. as an agonist, a partial agonist, as an antagonist or a partial antagonist). The fluorescence read out could either be produced within the cell or in an assay external to the cell and within the microdroplet.

In these situations it is advantageous to illuminate the whole of the microdroplet using laser light from an optical fibre. As with the light scattering examples described, the light may either be collected using the same optical fibre or alternatively at, say, 90 degrees to the light source (for example using a microscope objective).

For both cell-proliferation assays and fluorescence detection it can be useful to regulate the production of the emulsion so that the droplet volumes are all substantially the same (monodispersed). This can be achieved by detecting a flow rate of the microdroplets using the scattered light from the cells and/or scattered light from the droplet boundaries. In the latter case conveniently the same fibre optic may be employed for both counting cells and counting droplets, for example employing two different wavelengths for the two counting systems. The skilled person will also appreciate that regulation of droplet volume may be performed independently of whether or not the system is configured to look inside droplets to count cells.

Figure 8:
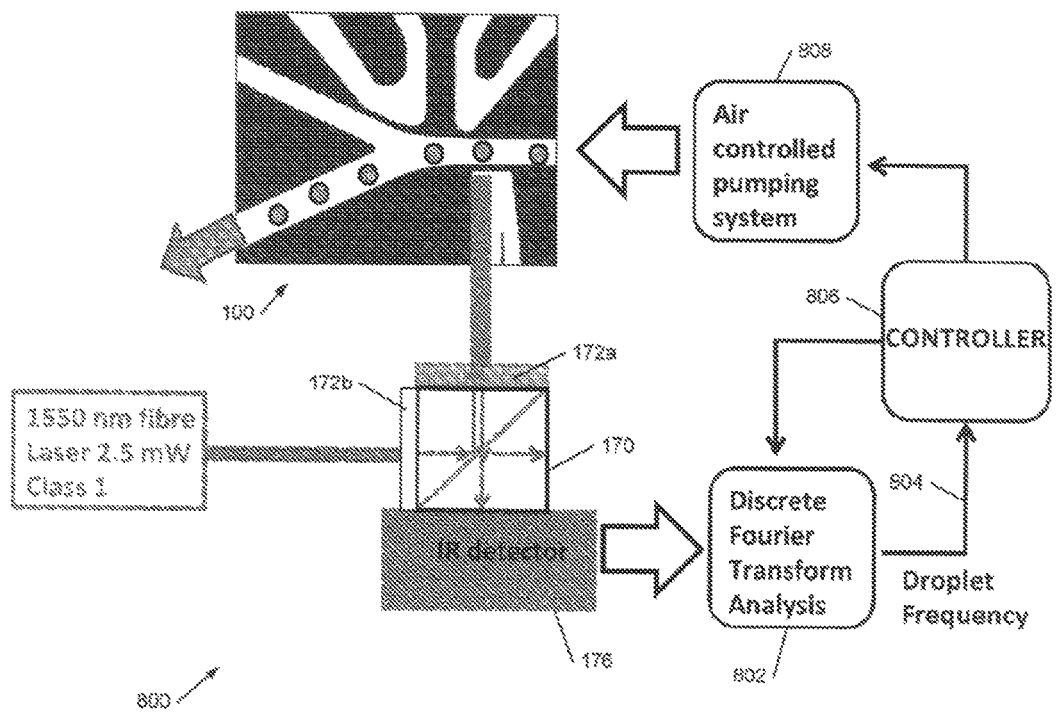
FIG. 8 illustrates a control system for a microfluidic device according to an embodiment of the invention.

Referring to FIG. 8 this shows a system [800] for regulating the microdroplet volume; like elements to those previously described that indicate by like reference numerals. Thus in the arrangement of FIG. 8 there is sufficient refractive index mismatch between the oil and water for the droplet boundaries to be identifiable in the signal from detector [176]. As illustrated the system employs an infrared laser but the skilled person will appreciate that in principle any wavelength may be employed. In principle a wavelength for viewing droplets may be chose to be one at which there is a greater index mismatch than at a wavelength used for counting cells.

Figure 9A:
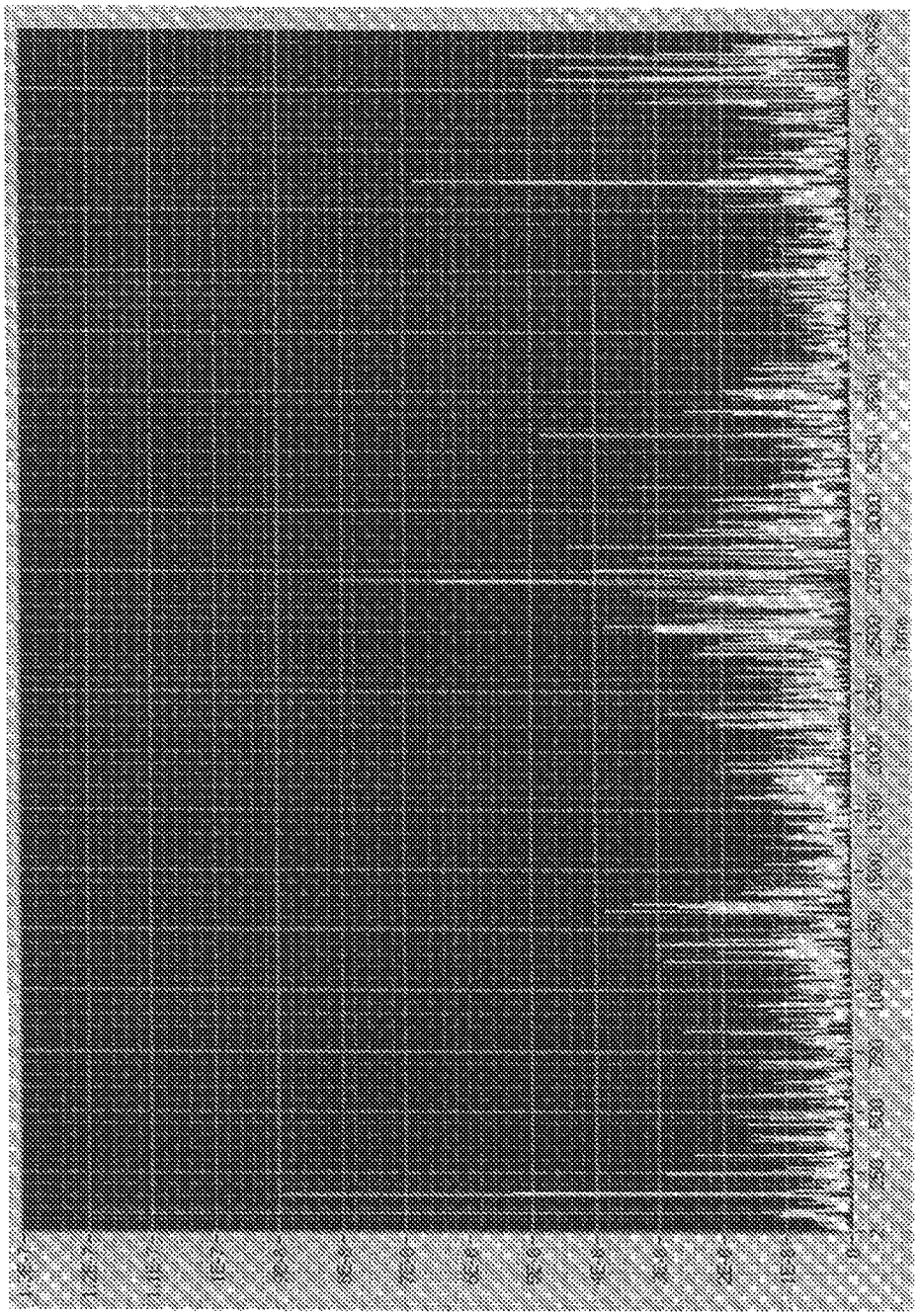
FIGS. 9*a* and 9*b* show, respectively, back-scattered light from microdroplets within a device of the type illustrated in FIG. 3, and a Fourier transform of the back-scattered light data showing the droplet frequency.
Figure 9B:
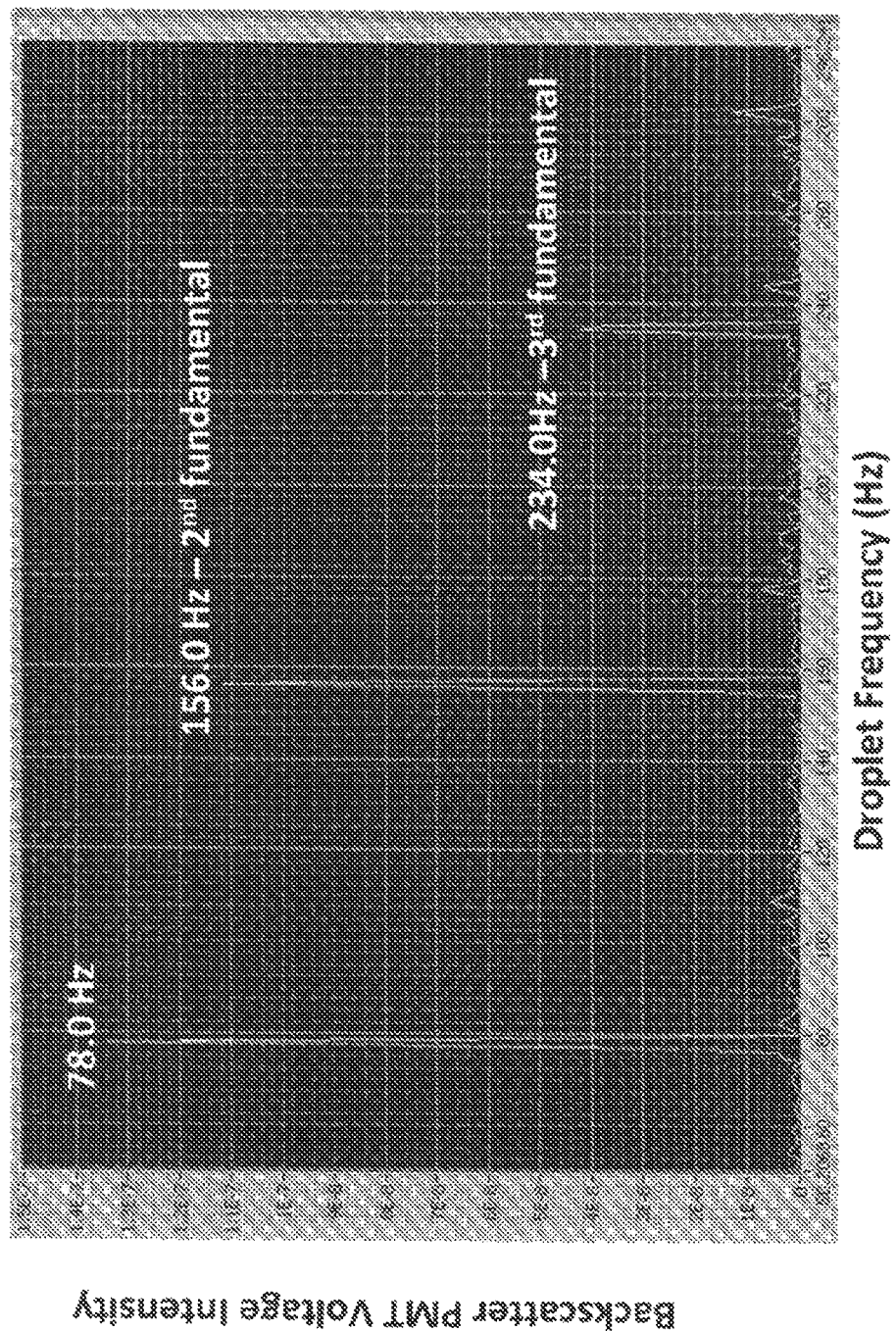

FIG. 9a illustrates an example signal from detector [176] which, as can be seen, is very small (of order 0.1 μV) and noisy. In preferred embodiments, therefore, the signal is converted to the frequency domain, for example by a discrete Fourier transform module [802] which provides a droplet frequency signal [804] to a controller [806]. A Fourier transformed version of a signal of a type shown in FIG. 9a is illustrated in FIG. 9b and, as can be seen, is very much cleaner. Only the fundamental frequency from the spectrum need be used.

Controller [806] controls a pumping system [808], in an experimental example an air-controlled pumping system broadly analogous to a syringe pump with a pumping rate controlled by air pressure. This is used to adjust a flow rate of the aqueous medium into the emulsion generation part of the system (in FIG. 3a, the flow focus junction), but it will be appreciated that additionally or alternatively the flow rate of the oil may also be controlled. In this way the droplet volume can be adjusted based on the detected flow rate so that the droplet volumes are substantially monodispersed. The skilled person will appreciate that the above described Fourier transform based approach will extract the fundamental frequency from time series data of cell detection signals even where cells are not present in every droplet, and this can therefore be applied whether or not there is a signal from a droplet boundary.

EXAMPLES

Example 1

Proof of concept experiments have been performed to generate and test clear and nearly clear emulsions by refractive index matching of the continuous phase (Pico-Surf™ 1 in Novec-7500, containing various proportions of refractive index modifying compounds with refractive indices higher than water) with the aqueous phase (DMEM-culture medium containing 10% Ficoll, which has an unknown refractive index). The chosen refractive index modifying compounds were all liquids. As there is only a low percentage of fluorous surfactant in the fluorous oil, we assume this will have a negligible effect on the refractive index of the pure fluorous oil.

An equation for the theoretical design of a clear emulsion is described by Sun et al (Refractive index matching and clear emulsions. Sun, J. Z., Erickson, C. E. and Parr, J. W. J. Cosmet. Sci., 56, 253-265, 2005).

Clear emulsion occurs when, $RI_{oil}=RI_{water}$

Refractive Index of the oil=$RI_{oil}=[\Sigma W_i \times n_i]/[\Sigma W_i]$ $W_i$=weight of each component, $n_i$=refractive index for each component Similarly Refractive Index of the water=$RI_{water}=[\Sigma W_i \times n_i]/[\Sigma W_i]$ However there are a number of limitations to this approach: i) No chemical reactions should take place between the constituents either in the phase to which it is dissolved or with a constituent in the other phase—this includes a neutralisation reaction; and ii) Ingredients in the oil phase should be physically insoluble in the water phase and vice versa.

The refractive index modifying compounds that were used for the proof of concept experiment were 1,3-bis-(trifluoromethyl)benzene (RI 1.379), 3-bromobenzotrifluoride (RI 1.473) and 1,1,1-trifluorotolune (RI 1.414). Other compounds could also be used, e.g. 1,3-bis-(trifluoromethyl)-5-bromenzene (RI 1.427), 3-iodobenzotrifluoride (RI 1.517) and 4-chloro-3-iodobenzene (RI 1.54).

The emulsion was generated first by vortexing DMEM culture medium containing 10% Ficoll (100 μL) with the modified 2% PicoSurf™ 1 Novec 7500 solution (300 μL). It was observed that the boundary interface almost disappeared with the solution comprising 30% wt 3-bromobenzotrifluoride in Novec 7500 (70% wt) and having a calculated refractive index of 1.343; assuming the RI of PicoSurf™ 1 in Novec7500 is the same as the pure fluorous oil. The solution with the clearest looking emulsion was re-tested using a droplet generator.

Example 2

An experiment to match the following aqueous solution was conducted in a droplet generator:

$D_2O$—RI 1.3284;
$H_2O$—RI 1.333;
Dulbecco's phosphate bufferered saline;
10% Ficoll in DMEM; and
LB bacterial growth medium.

Figure 10:
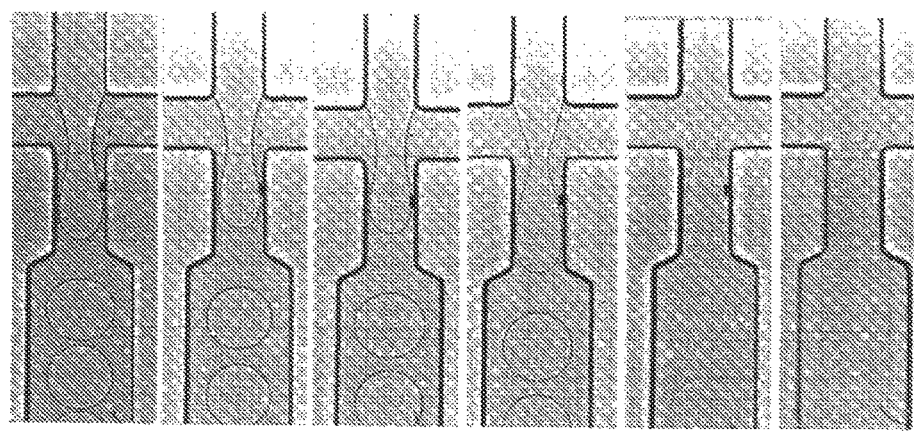
FIG. 10 shows the result of an example refractive index matching experiment.

The oil comprised of perfluorophenanthrene (PFP), 2% Pico-Surf™ 1 and various amounts of the refractive index modifying compound, 1,3-bis-trifluoromethyl-5-bromobenzene. From left to right in the image of FIG. 10, the percentage 1,3-bis-trifluoromethyl-5-bromobenzene was: 0%, 2.58%, 7.43%, 7.66%, 8.06% and 8.94%.

Applications of the above-described technques include, but are limited to, improved label-free cell sorting, and pre-sorting of empty microdroplets from microdroplets containing cells or particles; embodiments of the techniques can also be employed in flow cytometers, cell counters, imaging and microscopy. Embodiments of the techniques can still further be employed to provide signal enhancement of the fluorescence signal of both homogeneous and non-homogeneous fluorescence assays screened in microdroplets, e.g. fluorescence, FRET, or a TR-FRET assay, because of the increased optical transparency of the microdroplet. Thus embodiments of the technques can provide improved fluorescence activated cell sorter (FACS) systems, cell counters, imaging and microscopy.

No doubt many other effective alternatives will occur to the skilled person. It will be understood that the invention is not limited to the described embodiments and encompasses modifications apparent to those skilled in the art lying within the spirit and scope of the claims appended hereto.

What is claimed is:

1. A method of label-free cell or particle sorting or assaying in a microfluidic device, the method comprising:
providing a stream of aqueous droplets in oil in a channel of said microfluidic device, wherein at least some of said droplets include unlabeled cells or particles;
illuminating said stream from a first direction;
detecting light from unlabeled cells or particles within said aqueous droplets in a second direction;
determining a property of said cells or particles in each droplet from said detected light, wherein said step of determining includes determining the number of said cells or particles in each droplet by determining an integrated intensity of said light over time, and determining at least whether said number of unlabeled cells or particles falls above or below a threshold; and
sorting said aqueous droplets into one of a plurality of differentiated streams responsive to said determined number of said unlabeled cells or particles;
the method further comprising modifying a refractive index of said oil to more closely match a refractive index of said aqueous droplets, such that a difference between the refractive index of the modified oil and a refractive index of said aqueous droplets is less than a difference between the refractive index of the unmodified oil and a refractive index of the aqueous droplets, to reduce light scattered from boundaries of said droplets.

2. The method as claimed in claim 1, further comprising differentiating between live and dead cells based on their reflectance of light.

3. The method as claimed in claim 1, wherein determining of said property further comprises performing a fluorescence assay on said cells or particles.

4. The method as claimed in claim 1 wherein said oil is a fluorous oil, and wherein said aqueous droplet comprises a growth medium for said cells.

5. The method as claimed in claim 1, wherein said illuminating or detecting comprises illuminating or detecting using a fiber optic to illuminate or detect light from substantially an entire cross-section of a droplet.

6. The method as claimed in claim 1 wherein the modifying of the refractive indices comprises substantially matching said refractive indices to within 0.005.

7. The method as claimed in claim 1 comprising modifying a refractive index of said oil to more closely match a refractive index of said aqueous droplets, such that the difference between the refractive index of the modified oil and the refractive index of said aqueous droplets is less than the difference between the refractive index of the unmodified oil and the aqueous droplets, but without substantially matching said refractive indices within 0.005.

8. A method of label-free cell or particle sorting or assaying in a microfluidic device, the method comprising:
providing a stream of aqueous droplets in oil in a channel of said microfluidic device, wherein at least some of said droplets include unlabeled cells and/or particles;
illuminating said stream from a first direction;
detecting light from unlabeled cells or particles within said aqueous droplets in a second direction;
determining a property of said unlabeled cells or particles in each droplet from said detected light; and
sorting said aqueous droplets into one of a plurality of differentiated streams responsive to said determined property of said unlabeled cells or particles;
the method further comprising modifying a refractive index of said oil to more closely match a refractive index of said aqueous droplets, such that a difference between the refractive index of the modified oil and a refractive index of said aqueous droplets is less than a difference between the refractive index of the unmodified oil and a refractive index of the aqueous droplets, to reduce light scattered from boundaries of said droplets; and
further comprising determining, using said detected light or a further detected scattered light from said stream of aqueous droplets, a rate of passage of said aqueous droplets in said stream past a point in said channel, and controlling a volume of said droplets responsive to said determined rate of passage by performing a time-frequency domain transform on a signal from said detected light or said further detected scattered light.

9. The method as claimed in claim 8 wherein said step of determining said property of said unlabeled cells or particles in each droplet from said detected light further comprises visualizing and counting a number of cells/particles within said droplets.

10. The method as claimed in claim 8 wherein said controlling comprises controlling a flow rate of said oil or an aqueous medium into a flow focus junction of said device.

11. A method of performing an assay in a channel of a microfluidic device, the method comprising:
providing a stream of aqueous droplets in oil in a channel of said microfluidic device, wherein at least some of said droplets include entities;
detecting light from said droplets or from said entities within said droplets;
performing said assay on the entities within said droplets using said detected light by index matching refractive indices of said aqueous droplets and oil;
determining a flow rate of said droplets by performing a time-frequency domain transform on a signal from said light; and
controlling a volume of said droplets using both said detected light and said determined flow rate.

12. The method as claimed in claim 11, wherein said assay is a proliferation assay comprising visualizing and counting said entities within said droplets, and wherein said entities comprise cells.

13. The method as claimed in claim 11, wherein said assay is a cell viability assay comprising visualizing and counting said entities within said droplets, and wherein said entities comprise cells.

* * * * *